US012661398B2

(12) United States Patent
Ozawa et al.

(10) Patent No.: US 12,661,398 B2
(45) Date of Patent: Jun. 23, 2026

(54) COMBINATION OF A PD-1 ANTAGONIST, A VEGFR/FGFR/RET TYROSINE KINASE INHIBITOR AND A CBP/BETA-CATENIN INHIBITOR FOR TREATING CANCER

(71) Applicants: Eisai R&D Management Co., Ltd., Tokyo (JP); Merck Sharp & Dohme Corp., Rahway, NJ (US); MSD International GmbH, Lucerne (CH)

(72) Inventors: Yoichi Ozawa, Tsukuba (JP); Yasuhiro Funahashi, Tsukuba (JP); Yu Kato, Tsukuba (JP)

( * ) Notice: Subject to any disclaimer, the term of this patent is extended or adjusted under 35 U.S.C. 154(b) by 1054 days.

(21) Appl. No.: 17/772,468

(22) PCT Filed: Oct. 28, 2020

(86) PCT No.: PCT/US2020/057650
§ 371 (c)(1),
(2) Date: Apr. 27, 2022

(87) PCT Pub. No.: WO2021/086909
PCT Pub. Date: May 6, 2021

(65) Prior Publication Data

US 2022/0409724 A1 Dec. 29, 2022

Related U.S. Application Data

(60) Provisional application No. 62/927,334, filed on Oct. 29, 2019, provisional application No. 62/927,576, filed on Oct. 29, 2019.

(51) Int. Cl.
*A61K 39/395* (2006.01)
*A61K 31/47* (2006.01)
*A61K 31/53* (2006.01)
*A61P 35/00* (2006.01)

(52) U.S. Cl.
CPC .......... *A61K 39/3955* (2013.01); *A61K 31/47* (2013.01); *A61K 31/53* (2013.01); *A61P 35/00* (2018.01)

(58) Field of Classification Search
CPC .... A61K 39/3955; A61K 31/47; A61K 31/53; A61K 2039/505; A61K 45/06; A61K 2039/545; A61K 2300/00; A61P 35/00; C07K 16/2818
See application file for complete search history.

(56) References Cited

U.S. PATENT DOCUMENTS

| | | | |
|---|---|---|---|
| 9,174,998 | B2 | 11/2015 | Inoue et al. |
| 10,259,817 | B2 | 4/2019 | Kushida et al. |
| 2018/0185395 | A1 | 7/2018 | Odagami et al. |

FOREIGN PATENT DOCUMENTS

| | | | |
|---|---|---|---|
| CA | 3044658 A1 | 8/2018 | |
| WO | WO-2016/141218 A1 | 9/2016 | |
| WO | WO-2018/147275 A1 | 8/2018 | |

OTHER PUBLICATIONS

Broderick JM. FDA Grants Pembrolizumab/Lenvatinib Breakthrough Designation for RCC (https://www.onclive.com/view/fda-grants-pembrolizumablenvatinib-breakthrough-designation-for-rcc, Jan. 9, 2018) (Year: 2018).*

Luke JJ et al. Correlation of WNT/β-catenin pathway activation with immune exclusion across most human cancers. (Journal of Clinical Oncology 2016 34(15), Supp 1Abstract No. 3004.) (Year: 2016).*

Lee C. et al. A phase 1 b/2 trial of Lenvatinib plus pembrolizumab in patients with renal cell carcinoma. (Annals of Oncology 2017 28 (Supplement 5): v295-v329, ESMO 2017; Abstract 847O) (Year: 2017).*

NCT02501096. A Trial of Lenvatinib (E7080) Plus Pembrolizumab in Participants With Selected Solid Tumors. (https://clinicaltrials.gov/study/NCT02501096?term=NCT02501096&rank=1&tab=history&a=15#version-content-panel, Jan. 4, 2018 version) ( Year: 2018).*

Lala M et al. A six-weekly (Q6W) dosing schedule for pembrolizumab based on an exposure-response (E-R) evaluation using modeling and simulation. (Journal of Clinical Oncology 2018 36(15 suppl) abstract 3062) (Year: 2018).*

Adachi et al., E7386, a selective inhibitor of the interaction between [beta]-catenin and CREB-binding protein (CBP), enhances antitumor activity in combination with Lenvatinib (LEN), and LEN + anti-PD-1 antibody in a preclinical tumor model, Cancer Research, 83(7_Supplement):1837 (Apr. 4, 2023).

Grunwald et al., Lenvatinib plus everolimus or pembrolizumab versus sunitinib in advanced renal cell carcinoma: study design and rationale, Future Oncology, 15(9):929-941 (Mar. 2019).

Lee et al., 1187PD—Phase II study of lenvatinib plus pembrolizumab for disease progression after PD-1/PD-L1 immune checkpoint inhibitor in metastatic clear cell renal cell carcinoma (mccRCC): Results of an interim analysis, Immunotherapy of Cancer, 30(5):v483-v484 (Oct. 5, 2019).

(Continued)

*Primary Examiner* — Karen A. Canella
*Assistant Examiner* — John J Skoko, III
(74) *Attorney, Agent, or Firm* — MARSHALL, GERSTEIN & BORUN LLP

(57) ABSTRACT

The present disclosure describes a combination therapy comprising an antagonist of Programmed Death 1 receptor (PD-1), a lenvatinib or a pharmaceutically acceptable salt thereof, and (6S,9aS)-N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide (E7386) or a pharmaceutically acceptable salt thereof, —and the use of the combination therapies for the treatment of a cancer.

9 Claims, 17 Drawing Sheets

Specification includes a Sequence Listing.

(56) References Cited

OTHER PUBLICATIONS

Makker et al., Lenvatinib plus pembrolizumab in patients with advanced endometrial cancer: an interim analysis of a multicentre, open-label, single-arm, phase 2 trial, The Lancet Oncology, 20(5):1-8 (Mar. 25, 2019).
Shen et al., E7386, a Wnt/[beta]-catenin signaling modulator, suppresses the differentiation of regulatory T cells in combination with Lenvatinib plus anti-PD-1 antibody, Cancer Research, 84(6_ Supplement):2022 (Mar. 22, 2024).
Hori et al., E7386, an orally active CBP/beta-catenin modulator, induces T cells infiltration into tumor and enhances antitumor activity of anti-PD-1 mAb in Wnt1 tumor syngeneic mice model, Cancer Research, Abstract 5172, (2017).
Sharpe, et al., The function of programmed cell death 1 and its ligands in regulating autoimmunity and infection. *Nature Immunology*, 8:239-245, (2007).
Dong, et al., Tumor-associated B7-H1 promotes T-cell apoptosis: a potential mechanism of immune evasion, Nat Med, 8(8):793-800, (Aug. 2002).
Yang et al., PD-1 interaction contributes to the functional suppression of T-cell responses to human uveal melanoma cells in vitro, Invest. Ophthalmol. Vis. Sci., 49(6): 2518-2525, (2008).
Ghebeh et al., The B7-H1 (PD-L1) T lymphocyte-inhibitory molecule is expressed in breast cancer patients with infiltrating ductal carcinoma: correlation with important high-risk prognostic factors, *Neoplasia*, 8: 190-198, (2006).
Hamanishi et al., Programmed cell death 1 ligand 1 and tumor-infiltrating CD8+ T lymphocytes are prognostic factors of human ovarian cancer, Proc. Natl. Acad. Sci., 104: 3360-3365, (2007).
Thompson et al., Significance of B7-H1 overexpression in kidney cancer, Clinical genitourin Cancer, 5: 206-211, (2006).
Nomi et al., Clinical significance and therapeutic potential of the programmed death-1 ligand/programmed death-1 pathway in human pancreatic cancer, Clinical Cancer Research, 13: 2151-2157, (2007).
Ohigashi et al., Clinical significance of programmed death-1 ligand-1 and programmed death-1 ligand 2 expression in human esophageal cancer, *Clin. Cancer Research*, 11: 2947-2953, (2005).
Inman et al., PD-L1 (B7-H1) expression by urothelial carcinoma of the bladder and BCG-induced granulomata: associations with localized stage progression, Cancer, 109: 1499-1505, (2007).
Shimauchi et al., Augmented expression of programmed death-1 in both neoplasmatic and nonneoplastic CD4+ T-cells in adult T-cell Leukemia/ Lymphoma, *Int. J. Cancer*, 121: 2585-2590, (2007).
Gao et al., Overexpression of PD-L1 significantly associates with tumor aggressiveness and postoperative recurrence in human hepatocellular carcinoma, *Clinical Cancer Research*, 15: 971-979, (2009).
Nakanishi et al., Overexpression of B7-H1 (PD-L1) significantly associates with tumor grade and postoperative prognosis in human urothelial cancers, *Cancer Immunol. Immunother.*, 56: 1173-1182, (2007).
Hino et al., Tumor cell expression of programmed cell death-1 ligand 1 is a prognostic factor for malignant melanoma, Cancer, 1757-1766, (2010).
Ghebeh et al., Foxp3+ tregs and B7-H1+/PD-1+ T lymphocytes co-infiltrate the tumor tissues of high-risk breast cancer patients: implication for immunotherapy, *BMC Cancer*, 8: 57, (2008).
Ahmadzadeh et al., Tumor antigen-specific CD8 T cells infiltrating the tumor express high levels of PD-1 and are functionally impaired, *Blood*, 114: 1537-1544, (2009).
Thompson et al., PD-1 is expressed by tumor infiltrating cells and is associated with poor outcome for patients with renal carcinoma, *Clinical Cancer Research*, 15: 1757-1761, (2007).
Tamai et al., Suppressive expression of CD274 increases tumorigenesis and cancer stem cell phenotypes in cholangiocarcinoma, *Cancer Sci.* 105(6): 667-674, (2014).
El-Khoueiry et al., A phase I first-in-human study of PRI-724 in patients (pts) with advanced solid tumors, J. Clin. Oncol., 31(15): 2501, (May 2013).
Van Amerongen et al., Break the loop, escape the cycle?, *The EMBO Journal*, 32: 1977-1989, (2013).
Broderick, FDA grants Pembrolizumab/Lenvatinib breakthrough designation for RCC, OncLive (Jan. 2018).
Luke et al., Correlation of WNT/b-catenin pathway activation with immune exclusion across most human cancers, J. Clin. Oncol., 34(15): 3004, (2016).
Lee et al., A phase 1 b/2 trial of lenvatinib plus pembrolizumab in patients with renal cell carcinoma, Annals of Oncology, 28(5 Suppl.): v295-v296 (2017).
Eisai, Inc., NCT02501096: A Trial of Lenvatinib (E7080) Plus Pembrolizumab in Participants With Selected Solid Tumors, ClinicalTrials.gov, (Jul. 2023).

* cited by examiner

Figure 1 hPD-1.08A light chain CDR1 (SEQ ID NO: 1)

Arg Ala Ser Lys Ser Val Ser Thr Ser Gly Phe Ser Tyr Leu His hPD-1.08A light chain CDR2 (SEQ ID NO: 2)

Leu Ala Ser Asn Leu Glu Ser hPD-1.08A light chain CDR3 (SEQ ID NO: 3)

Gln His Ser Trp Glu Leu Pro Leu Thr hPD-1.08A heavy chain CDR1 (SEQ ID NO: 4)

Ser Tyr Tyr Leu Tyr hPD-1.08A heavy chain CDR2 (SEQ ID NO: 5)

Gly Val Asn Pro Ser Asn Gly Gly Thr Asn Phe Ser Glu Lys Phe Lys hPD-1.08A heavy chain CDR3 (SEQ ID NO: 6)

Arg Asp Ser Asn Tyr Asp Gly Gly Phe Asp Tyr

Figure 2 hPD-1.09A light chain CDR1 (SEQ ID NO: 7)

Arg Ala Ser Lys Gly Val Ser Thr Ser Gly Tyr Ser Tyr Leu His hPD-1.09A light chain CDR2 (SEQ ID NO: 8)

Leu Ala Ser Tyr Leu Glu Ser hPD-1.09A light chain CDR3 (SEQ ID NO: 9)

Gln His Ser Arg Asp Leu Pro Leu Thr hPD-1.09A heavy chain CDR1 (SEQ ID NO: 10)

Asn Tyr Tyr Met Tyr hPD-1.09 heavy chain CDR2 (SEQ ID NO: 11)

Gly Ile Asn Pro Ser Asn Gly Gly Thr Asn Phe Asn Glu Lys Phe Lys hPD-1.09 heavy chain CDR3 (SEQ ID NO: 12)

Arg Asp Tyr Arg Phe Asp Met Gly Phe Asp Tyr

Figure 3

109A-H heavy chain variable region (SEQ ID No: 13)

| | | | | | | | | | | | | | | |
|---|---|---|---|---|---|---|---|---|---|---|---|---|---|---|
| Gln | Val | Gln | Leu | Val | Gln | Ser | Gly | Val | Glu | Val | Lys | Lys | Pro | Gly |
| Ala | Ser | Val | Lys | Val | Ser | Cys | Lys | Ala | Ser | Gly | Tyr | Thr | Phe | Thr |
| Asn | Tyr | Tyr | Met | Tyr | Trp | Val | Arg | Gln | Ala | Pro | Gly | Gln | Gly | Leu |
| Glu | Trp | Met | Gly | Gly | Ile | Asn | Pro | Ser | Asn | Gly | Gly | Thr | Asn | Phe |
| Asn | Glu | Lys | Phe | Lys | Asn | Arg | Val | Thr | Leu | Thr | Thr | Asp | Ser | Ser |
| Thr | Thr | Thr | Ala | Tyr | Met | Glu | Leu | Lys | Ser | Leu | Gln | Phe | Asp | Asp |
| Thr | Ala | Val | Tyr | Tyr | Cys | Ala | Arg | Arg | Asp | Tyr | Arg | Phe | Asp | Met |
| Gly | Phe | Asp | Tyr | Trp | Gly | Gln | Gly | Thr | Thr | Val | Thr | Val | Ser | Ser |

409A-H heavy chain variable region (SEQ ID No: 14)

| | | | | | | | | | | | | | | |
|---|---|---|---|---|---|---|---|---|---|---|---|---|---|---|
| Gln | Val | Gln | Leu | Val | Gln | Ser | Gly | Val | Glu | Val | Lys | Lys | Pro | Gly |
| Ala | Ser | Val | Lys | Val | Ser | Cys | Lys | Ala | Ser | Gly | Tyr | Thr | Phe | Thr |
| Asn | Tyr | Tyr | Met | Tyr | Trp | Val | Arg | Gln | Ala | Pro | Gly | Gln | Gly | Leu |
| Glu | Trp | Met | Gly | Gly | Ile | Asn | Pro | Ser | Asn | Gly | Gly | Thr | Asn | Phe |
| Asn | Glu | Lys | Phe | Lys | Asn | Arg | Val | Thr | Leu | Thr | Thr | Asp | Ser | Ser |
| Thr | Thr | Thr | Ala | Tyr | Met | Glu | Leu | Lys | Ser | Leu | Gln | Phe | Asp | Asp |
| Thr | Ala | Val | Tyr | Tyr | Cys | Ala | Arg | Arg | Asp | Tyr | Arg | Phe | Asp | Met |
| Gly | Phe | Asp | Tyr | Trp | Gly | Gln | Gly | Thr | Thr | Val | Thr | Val | Ser | Ser |
| Ala | Ser | Thr | Lys | Gly | Pro | Ser | Val | Phe | Pro | Leu | Ala | Pro | Cys | Ser |
| Arg | Ser | Thr | Ser | Glu | Ser | Thr | Ala | Ala | Leu | Gly | Cys | Leu | Val | Lys |
| Asp | Tyr | Phe | Pro | Glu | Pro | Val | Thr | Val | Ser | Trp | Asn | Ser | Gly | Ala |
| Leu | Thr | Ser | Gly | Val | His | Thr | Phe | Pro | Ala | Val | Leu | Gln | Ser | Ser |
| Gly | Leu | Tyr | Ser | Leu | Ser | Ser | Val | Val | Thr | Val | Pro | Ser | Ser | Ser |
| Leu | Gly | Thr | Lys | Thr | Tyr | Thr | Cys | Asn | Val | Asp | His | Lys | Pro | Ser |
| Asn | Thr | Lys | Val | Asp | Lys | Arg | Val | Glu | Ser | Lys | Tyr | Gly | Pro | Pro |
| Cys | Pro | Pro | Cys | Pro | Ala | Pro | Glu | Phe | Leu | Gly | Gly | Pro | Ser | Val |
| Phe | Leu | Phe | Pro | Pro | Lys | Pro | Lys | Asp | Thr | Leu | Met | Ile | Ser | Arg |
| Thr | Pro | Glu | Val | Thr | Cys | Val | Val | Val | Asp | Val | Ser | Gln | Glu | Asp |
| Pro | Glu | Val | Gln | Phe | Asn | Trp | Tyr | Val | Asp | Gly | Val | Glu | Val | His |
| Asn | Ala | Lys | Thr | Lys | Pro | Arg | Glu | Glu | Gln | Phe | Asn | Ser | Thr | Tyr |
| Arg | Val | Val | Ser | Val | Leu | Thr | Val | Leu | His | Gln | Asp | Trp | Leu | Asn |
| Gly | Lys | Glu | Tyr | Lys | Cys | Lys | Val | Ser | Asn | Lys | Gly | Leu | Pro | Ser |
| Ser | Ile | Glu | Lys | Thr | Ile | Ser | Lys | Ala | Lys | Gly | Gln | Pro | Arg | Glu |
| Pro | Gln | Val | Tyr | Thr | Leu | Pro | Pro | Ser | Gln | Glu | Glu | Met | Thr | Lys |
| Asn | Gln | Val | Ser | Leu | Thr | Cys | Leu | Val | Lys | Gly | Phe | Tyr | Pro | Ser |
| Asp | Ile | Ala | Val | Glu | Trp | Glu | Ser | Asn | Gly | Gln | Pro | Glu | Asn | Asn |
| Tyr | Lys | Thr | Thr | Pro | Pro | Val | Leu | Asp | Ser | Asp | Gly | Ser | Phe | Phe |
| Leu | Tyr | Ser | Arg | Leu | Thr | Val | Asp | Lys | Ser | Arg | Trp | Gln | Glu | Gly |
| Asn | Val | Phe | Ser | Cys | Ser | Val | Met | His | Glu | Ala | Leu | His | Asn | His |
| Tyr | Thr | Gln | Lys | Ser | Leu | Ser | Leu | Ser | Leu | Gly | Lys | | | |

Figure 4

K09A-L-11 light chain variable region (SEQ ID No: 15)

| | | | | | | | | | | | | | | |
|---|---|---|---|---|---|---|---|---|---|---|---|---|---|---|
| Glu | Ile | Val | Leu | Thr | Gln | Ser | Pro | Ala | Thr | Leu | Ser | Leu | Ser | Pro |
| Gly | Glu | Arg | Ala | Thr | Leu | Ser | Cys | Arg | Ala | Ser | Lys | Gly | Val | Ser |
| Thr | Ser | Gly | Tyr | Ser | Tyr | Leu | His | Trp | Tyr | Gln | Gln | Lys | Pro | Gly |
| Gln | Ala | Pro | Arg | Leu | Leu | Ile | Tyr | Leu | Ala | Ser | Tyr | Leu | Glu | Ser |
| Gly | Val | Pro | Ala | Arg | Phe | Ser | Gly | Ser | Gly | Ser | Gly | Thr | Asp | Phe |
| Thr | Leu | Thr | Ile | Ser | Ser | Leu | Glu | Pro | Glu | Asp | Phe | Ala | Val | Tyr |
| Tyr | Cys | Gln | His | Ser | Arg | Asp | Leu | Pro | Leu | Thr | Phe | Gly | Gly | Gly |
| Thr | Lys | Val | Glu | Ile | Lys | | | | | | | | | |

K09A-L-16 light chain variable region (SEQ ID No: 16)

| | | | | | | | | | | | | | | |
|---|---|---|---|---|---|---|---|---|---|---|---|---|---|---|
| Glu | Ile | Val | Leu | Thr | Gln | Ser | Pro | Leu | Ser | Leu | Pro | Val | Thr | Pro |
| Gly | Glu | Pro | Ala | Ser | Ile | Ser | Cys | Arg | Ala | Ser | Lys | Gly | Val | Ser |
| Thr | Ser | Gly | Tyr | Ser | Tyr | Leu | His | Trp | Tyr | Leu | Gln | Lys | Pro | Gly |
| Gln | Ser | Pro | Gln | Leu | Leu | Ile | Tyr | Leu | Ala | Ser | Tyr | Leu | Glu | Ser |
| Gly | Val | Pro | Asp | Arg | Phe | Ser | Gly | Ser | Gly | Ser | Gly | Thr | Asp | Phe |
| Thr | Leu | Lys | Ile | Ser | Arg | Val | Glu | Ala | Glu | Asp | Val | Gly | Val | Tyr |
| Tyr | Cys | Gln | His | Ser | Arg | Asp | Leu | Pro | Leu | Thr | Phe | Gly | Gln | Gly |
| Thr | Lys | Leu | Glu | Ile | Lys | | | | | | | | | |

K09A-L-17 light chain variable region (SEQ ID No: 17)

| | | | | | | | | | | | | | | |
|---|---|---|---|---|---|---|---|---|---|---|---|---|---|---|
| Asp | Ile | Val | Met | Thr | Gln | Thr | Pro | Leu | Ser | Leu | Pro | Val | Thr | Pro |
| Gly | Glu | Pro | Ala | Ser | Ile | Ser | Cys | Arg | Ala | Ser | Lys | Gly | Val | Ser |
| Thr | Ser | Gly | Tyr | Ser | Tyr | Leu | His | Trp | Tyr | Leu | Gln | Lys | Pro | Gly |
| Gln | Ser | Pro | Gln | Leu | Leu | Ile | Tyr | Leu | Ala | Ser | Tyr | Leu | Glu | Ser |
| Gly | Val | Pro | Asp | Arg | Phe | Ser | Gly | Ser | Gly | Ser | Gly | Thr | Ala | Phe |
| Thr | Leu | Lys | Ile | Ser | Arg | Val | Glu | Ala | Glu | Asp | Val | Gly | Leu | Tyr |
| Tyr | Cys | Gln | His | Ser | Arg | Asp | Leu | Pro | Leu | Thr | Phe | Gly | Gln | Gly |
| Thr | Lys | Leu | Glu | Ile | Lys | | | | | | | | | |

Figure 5A

K09A-L-11 light chain full length (SEQ ID No: 18)

| | | | | | | | | | | | | | | |
|---|---|---|---|---|---|---|---|---|---|---|---|---|---|---|
| Glu | Ile | Val | Leu | Thr | Gln | Ser | Pro | Ala | Thr | Leu | Ser | Leu | Ser | Pro |
| Gly | Glu | Arg | Ala | Thr | Leu | Ser | Cys | Arg | Ala | Ser | Lys | Gly | Val | Ser |
| Thr | Ser | Gly | Tyr | Ser | Tyr | Leu | His | Trp | Tyr | Gln | Gln | Lys | Pro | Gly |
| Gln | Ala | Pro | Arg | Leu | Leu | Ile | Tyr | Leu | Ala | Ser | Tyr | Leu | Glu | Ser |
| Gly | Val | Pro | Ala | Arg | Phe | Ser | Gly | Ser | Gly | Ser | Gly | Thr | Asp | Phe |
| Thr | Leu | Thr | Ile | Ser | Ser | Leu | Glu | Pro | Glu | Asp | Phe | Ala | Val | Tyr |
| Tyr | Cys | Gln | His | Ser | Arg | Asp | Leu | Pro | Leu | Thr | Phe | Gly | Gly | Gly |
| Thr | Lys | Val | Glu | Ile | Lys | Arg | Thr | Val | Ala | Ala | Pro | Ser | Val | Phe |
| Ile | Phe | Pro | Pro | Ser | Asp | Glu | Gln | Leu | Lys | Ser | Gly | Thr | Ala | Ser |
| Val | Val | Cys | Leu | Leu | Asn | Asn | Phe | Tyr | Pro | Arg | Glu | Ala | Lys | Val |
| Gln | Trp | Lys | Val | Asp | Asn | Ala | Leu | Gln | Ser | Gly | Asn | Ser | Gln | Glu |
| Ser | Val | Thr | Glu | Gln | Asp | Ser | Lys | Asp | Ser | Thr | Tyr | Ser | Leu | Ser |
| Ser | Thr | Leu | Thr | Leu | Ser | Lys | Ala | Asp | Tyr | Glu | Lys | His | Lys | Val |
| Tyr | Ala | Cys | Glu | Val | Thr | His | Gln | Gly | Leu | Ser | Ser | Pro | Val | Thr |
| Lys | Ser | Phe | Asn | Arg | Gly | Glu | Cys | | | | | | | |

K09A-L-16 light chain full length (SEQ ID No: 19)

| | | | | | | | | | | | | | | |
|---|---|---|---|---|---|---|---|---|---|---|---|---|---|---|
| Glu | Ile | Val | Leu | Thr | Gln | Ser | Pro | Leu | Ser | Leu | Pro | Val | Thr | Pro |
| Gly | Glu | Pro | Ala | Ser | Ile | Ser | Cys | Arg | Ala | Ser | Lys | Gly | Val | Ser |
| Thr | Ser | Gly | Tyr | Ser | Tyr | Leu | His | Trp | Tyr | Leu | Gln | Lys | Pro | Gly |
| Gln | Ser | Pro | Gln | Leu | Leu | Ile | Tyr | Leu | Ala | Ser | Tyr | Leu | Glu | Ser |
| Gly | Val | Pro | Asp | Arg | Phe | Ser | Gly | Ser | Gly | Ser | Gly | Thr | Asp | Phe |
| Thr | Leu | Lys | Ile | Ser | Arg | Val | Glu | Ala | Glu | Asp | Val | Gly | Val | Tyr |
| Tyr | Cys | Gln | His | Ser | Arg | Asp | Leu | Pro | Leu | Thr | Phe | Gly | Gln | Gly |
| Thr | Lys | Leu | Glu | Ile | Lys | Arg | Thr | Val | Ala | Ala | Pro | Ser | Val | Phe |
| Ile | Phe | Pro | Pro | Ser | Asp | Glu | Gln | Leu | Lys | Ser | Gly | Thr | Ala | Ser |
| Val | Val | Cys | Leu | Leu | Asn | Asn | Phe | Tyr | Pro | Arg | Glu | Ala | Lys | Val |
| Gln | Trp | Lys | Val | Asp | Asn | Ala | Leu | Gln | Ser | Gly | Asn | Ser | Gln | Glu |
| Ser | Val | Thr | Glu | Gln | Asp | Ser | Lys | Asp | Ser | Thr | Tyr | Ser | Leu | Ser |
| Ser | Thr | Leu | Thr | Leu | Ser | Lys | Ala | Asp | Tyr | Glu | Lys | His | Lys | Val |
| Tyr | Ala | Cys | Glu | Val | Thr | His | Gln | Gly | Leu | Ser | Ser | Pro | Val | Thr |
| Lys | Ser | Phe | Asn | Arg | Gly | Glu | Cys | | | | | | | |

Figure 5B

K09A-L-17 light chain full length (SEQ ID No: 20)

| | | | | | | | | | | | | | | |
|---|---|---|---|---|---|---|---|---|---|---|---|---|---|---|
| Asp | Ile | Val | Met | Thr | Gln | Thr | Pro | Leu | Ser | Leu | Pro | Val | Thr | Pro |
| Gly | Glu | Pro | Ala | Ser | Ile | Ser | Cys | Arg | Ala | Ser | Lys | Gly | Val | Ser |
| Thr | Ser | Gly | Tyr | Ser | Tyr | Leu | His | Trp | Tyr | Leu | Gln | Lys | Pro | Gly |
| Gln | Ser | Pro | Gln | Leu | Leu | Ile | Tyr | Leu | Ala | Ser | Tyr | Leu | Glu | Ser |
| Gly | Val | Pro | Asp | Arg | Phe | Ser | Gly | Ser | Gly | Ser | Gly | Thr | Ala | Phe |
| Thr | Leu | Lys | Ile | Ser | Arg | Val | Glu | Ala | Glu | Asp | Val | Gly | Leu | Tyr |
| Tyr | Cys | Gln | His | Ser | Arg | Asp | Leu | Pro | Leu | Thr | Phe | Gly | Gln | Gly |
| Thr | Lys | Leu | Glu | Ile | Lys | Arg | Thr | Val | Ala | Ala | Pro | Ser | Val | Phe |
| Ile | Phe | Pro | Pro | Ser | Asp | Glu | Gln | Leu | Lys | Ser | Gly | Thr | Ala | Ser |
| Val | Val | Cys | Leu | Leu | Asn | Asn | Phe | Tyr | Pro | Arg | Glu | Ala | Lys | Val |
| Gln | Trp | Lys | Val | Asp | Asn | Ala | Leu | Gln | Ser | Gly | Asn | Ser | Gln | Glu |
| Ser | Val | Thr | Glu | Gln | Asp | Ser | Lys | Asp | Ser | Thr | Tyr | Ser | Leu | Ser |
| Ser | Thr | Leu | Thr | Leu | Ser | Lys | Ala | Asp | Tyr | Glu | Lys | His | Lys | Val |
| Tyr | Ala | Cys | Glu | Val | Thr | His | Gln | Gly | Leu | Ser | Ser | Pro | Val | Thr |
| Lys | Ser | Phe | Asn | Arg | Gly | Glu | Cys | | | | | | | |

Figure 6

Pembrolizumab

Heavy chain (SEQ ID NO: 21)

```
QVQLVQSGVE VKKPGASVKV SCKASGYTFT NYYMYWVRQA PGQGLEWMGG 50
INPSNGGTNF NEKFKNRVTL TTDSSTTTAY MELKSLQFDD TAVYYCARRD 100
YRFDMGFDYW GQGTTVTVSS ASTKGPSVFP LAPCSRSTSE STAALGCLVK 150
DYFPEPVTVS WNSGALTSGV HTFPAVLQSS GLYSLSSVVT VPSSSLGTKT 200
YTCNVDHKPS NTKVDKRVES KYGPPCPPCP APEFLGGPSV FLFPPKPKDT 250
LMISRTPEVT CVVVDVSQED PEVQFNWYVD GVEVHNAKTK PREEQFNSTY 300
RVVSVLTVLH QDWLNGKEYK CKVSNKGLPS SIEKTISKAK GQPREPQVYT 350
LPPSQEEMTK NQVSLTCLVK GFYPSDIAVE WESNGQPENN YKTTPPVLDS 400
DGSFFLYSRL TVDKSRWQEG NVFSCSVMHE ALHNHYTQKS LSLSLGK    447
```

Light chain (SEQ ID NO: 22)

```
EIVLTQSPAT LSLSPGERAT LSCRASKGVS TSGYSYLHWY QQKPGQAPRL 50
LIYLASYLES GVPARFSGSG SGTDFTLTIS SLEPEDFAVY YCQHSRDLPL 100
TFGGGTKVEI KRTVAAPSVF IFPPSDEQLK SGTASVVCLL NNFYPREAKV 150
QWKVDNALQS GNSQESVTEQ DSKDSTYSLS STLTLSKADY EKHKVYACEV 200
THQGLSSPVT KSFNRGEC                                   218
```

Figure 7

Nivolumab

Heavy chain (SEQ ID NO: 23)

```
QVQLVESGGG VVQPGRSLRL DCKASGITFS NSGMHWVRQA PGKGLEWVAV 50
IWYDGSKRYY ADSVKGRFTI SRDNSKNTLF LQMNSLRAED TAVYYCATND 100
DYWGQGTLVT VSSASTKGPS VFPLAPCSRS TSESTAALGC LVKDYFPEPV 150
TVSWNSGALT SGVHTFPAVL QSSGLYSLSS VVTVPSSSLG TKTYTCNVDH 200
KPSNTKVDKR VESKYGPPCP PCPAPEFLGG PSVFLFPPKP KDTLMISRTP 250
EVTCVVVDVS QEDPEVQFNW YVDGVEVHNA KTKPREEQFN STYRVVSVLT 300
VLHQDWLNGK EYKCKVSNKG LPSSIEKTIS KAKGQPREPQ VYTLPPSQEE 350
MTKNQVSLTC LVKGFYPSDI AVEWESNGQP ENNYKTTPPV LDSDGSFFLY 400
SRLTVDKSRW QEGNVFSCSV MHEALHNHYT QKSLSLSLGK            440
```

Light chain (SEQ ID NO: 24)

```
EIVLTQSPAT LSLSPGERAT LSCRASQSVS SYLAWYQQKP GQAPRLLIYD 50
ASNRATGIPA RFSGSGSGTD FTLTISSLEP EDFAVYYCQQ SSNWPRTFGQ 100
GTKVEIKRTV AAPSVFIFPP SDEQLKSGTA SVVCLLNNFY PREAKVQWKV 150
DNALQSGNSQ ESVTEQDSKD STYSLSSTLT LSKADYEKHK VYACEVTHQG 200
LSSPVTKSFN RGEC                                        214
```

Figure 10A

| Cell line | A<br>Culture medium | B<br>Cell concentration | C<br>Animal strain | D<br>Start dosing (days after) | E<br>Dosing period |
|---|---|---|---|---|---|
| Renal cell carcinoma cell line **RAG** (ATCC number: CCL-142) | An Eagle's minimal essential medium (E-MEM) containing 10% fetal bovine serum (FBS) and penicillin/streptomycin (100 units/mL each) | $2.5 \times 10^7$ cells/mL | BALB/cAnNCrlCrlj, female, Charles River Laboratories Japan Inc. | 8 days | 4 weeks |
| Renal cell carcinoma cell line **Renca** (ATCC number: CRL-2947) | A RPMI1640 containing 10% fetal bovine serum (FBS), NEAA (0.1 mM), sodium pyruvate (1 mM), L-glutamine (2 mM) and penicillin/streptomycin (100 units/mL each) | $2 \times 10^7$ cells/mL | BALB/cAnNCrlCrlj, female, Charles River Laboratories Japan Inc. | 8 days | 3 weeks |
| Hepatoma cell line **Hepa1-6** (ATCC number: CRL-1830) | A Dulbecco's Modified Eagle's medium (DMEM) containing 10% fetal bovine serum (FBS) and penicillin/streptomycin (100 units/mL each) | $4 \times 10^7$ cells/mL | C57L/J, male, Breeding in-house | 11 days | 4 weeks |
| Chemically transformed liver cell line **BNL 1ME A.7R.1** (ATCC number: TIB-75) | A Dulbecco's Modified Eagle's medium (DMEM) containing 10% fetal bovine serum (FBS) and penicillin/streptomycin (100 units/mL each) | $1.4 \times 10^8$ cells/mL | BALB/cAnNCrlCrlj, male, Charles River Laboratories Japan Inc. | 4 days | 4 weeks |

Figure 10B

| Cell line | A<br>Culture medium | B<br>Cell concentration | C<br>Animal strain | D<br>Start dosing (days after) | E<br>Dosing period |
|---|---|---|---|---|---|
| Colon carcinoma cell line **CT26.WT** (ATCC number: CRL-2638) | A RPMI1640 containing 10% fetal bovine serum (FBS) and penicillin/streptomycin (100 units/mL each) | 1 x $10^7$ cells/mL | BALB/cAnNCrlCrlj, female, Charles River Laboratories Japan Inc. | 4 days | 3 weeks |
| Colon adenocarcinoma cell line **MC38** (Kerafast Cat#: ENH204-FP) | A Dulbecco's Modified Eagle's medium (DMEM) containing 10% fetal bovine serum (FBS) and penicillin/streptomycin (100 units/mL each) | 2 x $10^7$ cells/mL | C57BL/6NCrl, female, Charles River Laboratories Japan Inc. | 7 days | 4 weeks |
| Breast cancer cell line **4T1** (ATCC number: CRL-2539) | A RPMI1640 (ATCC-30-2001) containing 10% fetal bovine serum (FBS) and penicillin/streptomycin (100 units/mL each) | 5 x $10^7$ cells/mL | BALB/cAnNCrlCrlj, female, Charles River Laboratories Japan Inc. | 5 days | 3 weeks |
| Mammary carcinoma cell line **EMT6** (ATCC number: CRL-2755) | A Waymouth's (1x) MB752/1 medium containing 15% fetal bovine serum (FBS), 1x GlutaMAX-1 and penicillin/streptomycin (100 units/mL each) | 5 x $10^7$ cells/mL | BALB/cAnNCrlCrlj, female, Charles River Laboratories Japan Inc. | 6 days | 3 weeks |

Figure 10C

| Cell line | A<br>Culture medium | B<br>Cell concentration | C<br>Animal strain | D<br>Start dosing (days after) | E<br>Dosing period |
|---|---|---|---|---|---|
| Lung squamous cell carcinoma cell line **KLN205** (ATCC number: CRL-1453) | An Eagle's minimal essential medium (E-MEM) containing 10% fetal bovine serum (FBS), sodium pyruvate (1 mM) and penicillin/streptomycin (100 units/mL each) | 2 x $10^7$ cells/mL | DBA/2NCrl, female, Charles River Laboratories Japan Inc. | 7 days | 3 weeks |
| Lewis lung carcinoma cell line **LL2** (ATCC number: CRL-1642) | A Dulbecco's Modified Eagle's medium (DMEM) containing 10% fetal bovine serum (FBS) and penicillin/streptomycin (100 units/mL each) | 2 x $10^7$ cells/mL | C57BL/6JCrl, female, Charles River Laboratories Japan Inc. | 7 days | 3 weeks |
| Melanoma cell line **B16-F10** (ATCC number: CRL-6475) | A Dulbecco's Modified Eagle's medium (DMEM) containing 10% fetal bovine serum (FBS) and penicillin/streptomycin (100 units/mL each) | 5 x $10^7$ cells/mL | C57BL/6NCrl, female, Charles River Laboratories Japan Inc. | 4 days | 3 weeks |
| Bladder carcinoma cell line **MBT2** (JCRB number: IFO50041) | An Eagle's minimal essential medium (E-MEM) containing 10% fetal bovine serum (FBS) and penicillin/streptomycin (100 units/mL each) | 1 x $10^7$ cells/mL | C3H/HeNCrl, female, Charles River Laboratories Japan Inc. | 6 days | 4 weeks |

Figure 11

| No. | 1 | 2 | 3 | 4 | 5 | 6 | 7 | 8 | 9 | 10 | 11 | 12 |
|---|---|---|---|---|---|---|---|---|---|---|---|---|
| T/C Day 15 | Hepal-6 | RAG | MC38 | CT26.WT | MBT-2 | B16/F10 | Renca | BNL 1ME | KLN205 | 4T1 | LL2 | EMT6 |
| | HCC | RCC | Colon | Colon | Bladder | Melanoma | HCC | HCC | Lung | Breast | Lung | Breast |
| LEN 10 | 7% | 28% | 16% | 28% | 44% | 7% | 17% | -12% | 26% | 38% | 74% | 51% |
| PD-1Ab | 4% | 49% | 107% | 48% | 52% | 63% | 84% | 94% | 85% | 101% | 113% | 67% |
| LEN/PD-1 | -47% | 9% | 10% | 7% | 5% | 4% | 17% | -34% | 46% | 48% | 70% | 47% |
| Combination Effect | - | + | + | + | + | - | - | + | - | - | - | - |
| E7386 25 | 77% | 77% | 91% | 100% | 98% | 97% | 98% | 91% | 79% | 97% | 111% | 102% |
| E7386/LEN | -15% | 8% | 8% | 10% | 8% | 4% | 12% | -52% | 10% | 32% | 53% | 44% |
| Combination Effect | - | + | + | + | + | - | + | + | + | - | + | - |
| E7386/LEN/PD-1 | -64% | -47% | 6% | 3% | -41% | 2% | 8% | -70% | 7% | 25% | 58% | 46% |
| Combination Effect vs LEN/PD-1 | + | + | + | + | - | - | + | + | + | + | + | - |
| Combination Effect vs sE7386/LEN | + | + | + | + | + | + | + | + | - | + | - | - |

SEQUENCE LISTING

```
<160> NUMBER OF SEQ ID NOS: 25

<210> SEQ ID NO 1
<211> LENGTH: 15
<212> TYPE: PRT
<213> ORGANISM: Artificial Sequence
<220> FEATURE:
<223> OTHER INFORMATION: Antibody Light Chain CDR

<400> SEQUENCE: 1

Arg Ala Ser Lys Ser Val Ser Thr Ser Gly Phe Ser Tyr Leu His
1               5                   10                  15


<210> SEQ ID NO 2
<211> LENGTH: 7
<212> TYPE: PRT
<213> ORGANISM: Artificial Sequence
<220> FEATURE:
<223> OTHER INFORMATION: Antibody Light Chain CDR

<400> SEQUENCE: 2

Leu Ala Ser Asn Leu Glu Ser
1               5


<210> SEQ ID NO 3
<211> LENGTH: 9
<212> TYPE: PRT
<213> ORGANISM: Artificial Sequence
<220> FEATURE:
```

-continued

<223> OTHER INFORMATION: Antibody Light Chain CDR

<400> SEQUENCE: 3

Gln His Ser Trp Glu Leu Pro Leu Thr
1 5

<210> SEQ ID NO 4
<211> LENGTH: 5
<212> TYPE: PRT
<213> ORGANISM: Artificial Sequence
<220> FEATURE:
<223> OTHER INFORMATION: Antibody Heavy Chain CDR

<400> SEQUENCE: 4

Ser Tyr Tyr Leu Tyr
1 5

<210> SEQ ID NO 5
<211> LENGTH: 17
<212> TYPE: PRT
<213> ORGANISM: Artificial Sequence
<220> FEATURE:
<223> OTHER INFORMATION: Antibody Heavy Chain CDR

<400> SEQUENCE: 5

Gly Val Asn Pro Ser Asn Gly Gly Thr Asn Phe Ser Glu Lys Phe Lys
1 5 10 15

Ser

<210> SEQ ID NO 6
<211> LENGTH: 11
<212> TYPE: PRT
<213> ORGANISM: Artificial Sequence
<220> FEATURE:
<223> OTHER INFORMATION: Antibody Heavy Chain CDR

<400> SEQUENCE: 6

Arg Asp Ser Asn Tyr Asp Gly Gly Phe Asp Tyr
1 5 10

<210> SEQ ID NO 7
<211> LENGTH: 15
<212> TYPE: PRT
<213> ORGANISM: Artificial Sequence
<220> FEATURE:
<223> OTHER INFORMATION: Antibody Light Chain CDR

<400> SEQUENCE: 7

Arg Ala Ser Lys Gly Val Ser Thr Ser Gly Tyr Ser Tyr Leu His
1 5 10 15

<210> SEQ ID NO 8
<211> LENGTH: 7
<212> TYPE: PRT
<213> ORGANISM: Artificial Sequence
<220> FEATURE:
<223> OTHER INFORMATION: Antibody Light Chain CDR

<400> SEQUENCE: 8

Leu Ala Ser Tyr Leu Glu Ser
1 5

<210> SEQ ID NO 9
<211> LENGTH: 9
<212> TYPE: PRT
<213> ORGANISM: Artificial Sequence -continued
<220> FEATURE:
<223> OTHER INFORMATION: Antibody Light Chain CDR

<400> SEQUENCE: 9

Gln His Ser Arg Asp Leu Pro Leu Thr
1 5

<210> SEQ ID NO 10
<211> LENGTH: 5
<212> TYPE: PRT
<213> ORGANISM: Artificial Sequence
<220> FEATURE:
<223> OTHER INFORMATION: Antibody Heavy Chain CDR

<400> SEQUENCE: 10

Asn Tyr Tyr Met Tyr
1 5

<210> SEQ ID NO 11
<211> LENGTH: 17
<212> TYPE: PRT
<213> ORGANISM: Artificial Sequence
<220> FEATURE:
<223> OTHER INFORMATION: Antibody Heavy Chain CDR

<400> SEQUENCE: 11

Gly Ile Asn Pro Ser Asn Gly Gly Thr Asn Phe Asn Glu Lys Phe Lys
1 5 10 15

Asn

<210> SEQ ID NO 12
<211> LENGTH: 11
<212> TYPE: PRT
<213> ORGANISM: Artificial Sequence
<220> FEATURE:
<223> OTHER INFORMATION: Antibody Heavy Chain CDR

<400> SEQUENCE: 12

Arg Asp Tyr Arg Phe Asp Met Gly Phe Asp Tyr
1 5 10

<210> SEQ ID NO 13
<211> LENGTH: 120
<212> TYPE: PRT
<213> ORGANISM: Artificial Sequence
<220> FEATURE:
<223> OTHER INFORMATION: Humanized Antibody Heavy Chain Variable Region

<400> SEQUENCE: 13

Gln Val Gln Leu Val Gln Ser Gly Val Glu Val Lys Lys Pro Gly Ala
1 5 10 15

Ser Val Lys Val Ser Cys Lys Ala Ser Gly Tyr Thr Phe Thr Asn Tyr
20 25 30

Tyr Met Tyr Trp Val Arg Gln Ala Pro Gly Gln Gly Leu Glu Trp Met
35 40 45

Gly Gly Ile Asn Pro Ser Asn Gly Gly Thr Asn Phe Asn Glu Lys Phe
50 55 60

Lys Asn Arg Val Thr Leu Thr Thr Asp Ser Ser Thr Thr Thr Ala Tyr
65 70 75 80

Met Glu Leu Lys Ser Leu Gln Phe Asp Asp Thr Ala Val Tyr Tyr Cys
85 90 95

Ala Arg Arg Asp Tyr Arg Phe Asp Met Gly Phe Asp Tyr Trp Gly Gln
100 105 110

```
Gly Thr Thr Val Thr Val Ser Ser
        115                 120


<210> SEQ ID NO 14
<211> LENGTH: 447
<212> TYPE: PRT
<213> ORGANISM: Artificial Sequence
<220> FEATURE:
<223> OTHER INFORMATION: Humanized Antibody Heavy Chain

<400> SEQUENCE: 14

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350
```

-continued

```
Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445


<210> SEQ ID NO 15
<211> LENGTH: 111
<212> TYPE: PRT
<213> ORGANISM: Artificial Sequence
<220> FEATURE:
<223> OTHER INFORMATION: Humanized Antibody Light Chain Variable Region

<400> SEQUENCE: 15

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys
            100                 105                 110


<210> SEQ ID NO 16
<211> LENGTH: 111
<212> TYPE: PRT
<213> ORGANISM: Artificial Sequence
<220> FEATURE:
<223> OTHER INFORMATION: Humanized Antibody Light Chain Variable Region

<400> SEQUENCE: 16

Glu Ile Val Leu Thr Gln Ser Pro Leu Ser Leu Pro Val Thr Pro Gly
1               5                   10                  15

Glu Pro Ala Ser Ile Ser Cys Arg Ala Ser Lys Gly Val Ser Thr Ser
            20                  25                  30

Gly Tyr Ser Tyr Leu His Trp Tyr Leu Gln Lys Pro Gly Gln Ser Pro
        35                  40                  45

Gln Leu Leu Ile Tyr Leu Ala Ser Tyr Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Arg
                85                  90                  95

Asp Leu Pro Leu Thr Phe Gly Gln Gly Thr Lys Leu Glu Ile Lys
```

-continued

```
            100                 105                 110


<210> SEQ ID NO 17
<211> LENGTH: 111
<212> TYPE: PRT
<213> ORGANISM: Artificial Sequence
<220> FEATURE:
<223> OTHER INFORMATION: Humanized Antibody Light Chain Variable Regon

<400> SEQUENCE: 17

Asp Ile Val Met Thr Gln Thr Pro Leu Ser Leu Pro Val Thr Pro Gly
1               5                   10                  15

Glu Pro Ala Ser Ile Ser Cys Arg Ala Ser Lys Gly Val Ser Thr Ser
            20                  25                  30

Gly Tyr Ser Tyr Leu His Trp Tyr Leu Gln Lys Pro Gly Gln Ser Pro
        35                  40                  45

Gln Leu Leu Ile Tyr Leu Ala Ser Tyr Leu Glu Ser Gly Val Pro Asp
    50                  55                  60

Arg Phe Ser Gly Ser Gly Ser Gly Thr Ala Phe Thr Leu Lys Ile Ser
65                  70                  75                  80

Arg Val Glu Ala Glu Asp Val Gly Leu Tyr Tyr Cys Gln His Ser Arg
                85                  90                  95

Asp Leu Pro Leu Thr Phe Gly Gln Gly Thr Lys Leu Glu Ile Lys
            100                 105                 110


<210> SEQ ID NO 18
<211> LENGTH: 218
<212> TYPE: PRT
<213> ORGANISM: Artificial Sequence
<220> FEATURE:
<223> OTHER INFORMATION: Humanzed Antiboy Light Chain

<400> SEQUENCE: 18

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190
```

```
His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 19
<211> LENGTH: 218
<212> TYPE: PRT
<213> ORGANISM: Artificial Sequence
<220> FEATURE:
<223> OTHER INFORMATION: Humanized Antibody Light Chain

<400> SEQUENCE: 19

Glu Ile Val Leu Thr Gln Ser Pro Leu Ser Leu Pro Val Thr Pro Gly
1               5                   10                  15

Glu Pro Ala Ser Ile Ser Cys Arg Ala Ser Lys Gly Val Ser Thr Ser
            20                  25                  30

Gly Tyr Ser Tyr Leu His Trp Tyr Leu Gln Lys Pro Gly Gln Ser Pro
        35                  40                  45

Gln Leu Leu Ile Tyr Leu Ala Ser Tyr Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Arg
                85                  90                  95

Asp Leu Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 20
<211> LENGTH: 218
<212> TYPE: PRT
<213> ORGANISM: Artificial Sequence
<220> FEATURE:
<223> OTHER INFORMATION: Humanized Antibody Light Chain

<400> SEQUENCE: 20

Asp Ile Val Met Thr Gln Thr Pro Leu Ser Leu Pro Val Thr Pro Gly
1               5                   10                  15

Glu Pro Ala Ser Ile Ser Cys Arg Ala Ser Lys Gly Val Ser Thr Ser
            20                  25                  30

Gly Tyr Ser Tyr Leu His Trp Tyr Leu Gln Lys Pro Gly Gln Ser Pro
        35                  40                  45

Gln Leu Leu Ile Tyr Leu Ala Ser Tyr Leu Glu Ser Gly Val Pro Asp
    50                  55                  60
```

-continued

```
Arg Phe Ser Gly Ser Gly Ser Gly Thr Ala Phe Thr Leu Lys Ile Ser
65                  70                  75                  80

Arg Val Glu Ala Glu Asp Val Gly Leu Tyr Tyr Cys Gln His Ser Arg
                85                  90                  95

Asp Leu Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 21
<211> LENGTH: 447
<212> TYPE: PRT
<213> ORGANISM: Artificial Sequence
<220> FEATURE:
<223> OTHER INFORMATION: Humanized Antibody Heavy Chain

<400> SEQUENCE: 21

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205
```

```
Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445


<210> SEQ ID NO 22
<211> LENGTH: 218
<212> TYPE: PRT
<213> ORGANISM: Artificial Sequence
<220> FEATURE:
<223> OTHER INFORMATION: Humanized Antibody Light Chain

<400> SEQUENCE: 22

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125
```

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 23
<211> LENGTH: 440
<212> TYPE: PRT
<213> ORGANISM: Homo sapiens

<400> SEQUENCE: 23

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln

-continued

```
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440


<210> SEQ ID NO 24
<211> LENGTH: 214
<212> TYPE: PRT
<213> ORGANISM: Homo sapiens

<400> SEQUENCE: 24

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
Phe Asn Arg Gly Glu Cys
    210


<210> SEQ ID NO 25
<211> LENGTH: 290
<212> TYPE: PRT
<213> ORGANISM: Homo sapiens
<220> FEATURE:
<221> NAME/KEY: mat_peptide
<222> LOCATION: (19)..(290)

<400> SEQUENCE: 25

Met Arg Ile Phe Ala Val Phe Ile Phe Met Thr Tyr Trp His Leu Leu
            -15                 -10                 -5

Asn Ala Phe Thr Val Thr Val Pro Lys Asp Leu Tyr Val Val Glu Tyr
    -1  1               5                   10

Gly Ser Asn Met Thr Ile Glu Cys Lys Phe Pro Val Glu Lys Gln Leu
15                  20                  25                  30

Asp Leu Ala Ala Leu Ile Val Tyr Trp Glu Met Glu Asp Lys Asn Ile
                35                  40                  45

Ile Gln Phe Val His Gly Glu Glu Asp Leu Lys Val Gln His Ser Ser
            50                  55                  60

Tyr Arg Gln Arg Ala Arg Leu Leu Lys Asp Gln Leu Ser Leu Gly Asn
        65                  70                  75

Ala Ala Leu Gln Ile Thr Asp Val Lys Leu Gln Asp Ala Gly Val Tyr
    80                  85                  90

Arg Cys Met Ile Ser Tyr Gly Gly Ala Asp Tyr Lys Arg Ile Thr Val
95                  100                 105                 110

Lys Val Asn Ala Pro Tyr Asn Lys Ile Asn Gln Arg Ile Leu Val Val
                115                 120                 125

Asp Pro Val Thr Ser Glu His Glu Leu Thr Cys Gln Ala Glu Gly Tyr
            130                 135                 140

Pro Lys Ala Glu Val Ile Trp Thr Ser Ser Asp His Gln Val Leu Ser
        145                 150                 155

Gly Lys Thr Thr Thr Thr Asn Ser Lys Arg Glu Glu Lys Leu Phe Asn
    160                 165                 170

Val Thr Ser Thr Leu Arg Ile Asn Thr Thr Thr Asn Glu Ile Phe Tyr
175                 180                 185                 190

Cys Thr Phe Arg Arg Leu Asp Pro Glu Glu Asn His Thr Ala Glu Leu
                195                 200                 205

Val Ile Pro Glu Leu Pro Leu Ala His Pro Pro Asn Glu Arg Thr His
            210                 215                 220

Leu Val Ile Leu Gly Ala Ile Leu Leu Cys Leu Gly Val Ala Leu Thr
        225                 230                 235

Phe Ile Phe Arg Leu Arg Lys Gly Arg Met Met Asp Val Lys Lys Cys
    240                 245                 250

Gly Ile Gln Asp Thr Asn Ser Lys Lys Gln Ser Asp Thr His Leu Glu
255                 260                 265                 270

Glu Thr
```

COMBINATION OF A PD-1 ANTAGONIST, A VEGFR/FGFR/RET TYROSINE KINASE INHIBITOR AND A CBP/BETA-CATENIN INHIBITOR FOR TREATING CANCER

REFERENCE TO RELATED APPLICATIONS

This application is the National Stage of International Application No. PCT/US2020/057650 filed Oct. 28, 2020, which claims priority to and benefit of U.S. Provisional Application Nos. 62/927,334 and 62/927,576 both filed on Oct. 29, 2019, each of which is herein incorporated by reference in its entirety.

SEQUENCE LISTING

The instant application contains a Sequence listing which has been submitted electronically in ASCII format and is hereby incorporated by reference in its entirety. Said ASCII copy, created on Apr. 12, 2022, is named 213597-0005-00-US-SL.txt and is 31,564 bytes in size.

TECHNICAL FIELD

Combination therapies useful for the treatment of cancer are disclosed. A combination therapy which comprises an antagonist of a Programmed Death 1 (PD-1) protein, lenvatinib, a multi-receptor tyrosine kinase (multi-RTK) inhibitor, or a pharmaceutically acceptable salt thereof, and E7386, a CBP/β-catenin inhibitor that inhibits an interaction between CBP and β-catenin, or a pharmaceutically acceptable salt thereof, is disclosed. A tumor therapeutic agent containing a combination of an anti-PD-1 antibody, lenvatinib or a pharmaceutically acceptable salt thereof and E7386 or a pharmaceutically acceptable salt thereof is also disclosed.

BACKGROUND

PD-1 is recognized as an important player in immune regulation and the maintenance of peripheral tolerance. PD-1 is moderately expressed on naive T-, B- and Natural killer T (NKT)-cells and up-regulated by T/B-cell receptor signaling on lymphocytes, monocytes and myeloid cells (1).

Two known ligands for PD-1, PD-L1 (B7-H1) and PD-L2 (B7-DC), are expressed in human cancers arising in various tissues. In large sample sets of e.g. ovarian, renal, colorectal, pancreatic, liver cancers and melanoma, it was shown that PD-L1 expression correlated with poor prognosis and reduced overall survival irrespective of subsequent treatment (2-13). Similarly, PD-1 expression on tumor infiltrating lymphocytes was found to mark dysfunctional T cells in breast cancer and melanoma (14-15) and to correlate with poor prognosis in renal cancer (16). It has been proposed that PD-L1 expressing tumor cells interact with PD-1 expressing T cells to attenuate T cell activation and evasion of immune surveillance, thereby contributing to an impaired immune response against the tumor. Therefore, an antibody directed against either the PD-1 receptor or the PD-L1 ligand can inhibit the binding there between, resulting in an increased immune action on the tumor cells (23).

Several monoclonal antibodies that inhibit the interaction between PD-1 and one or both of its ligands PD-L1 and PD-L2 have been approved for use by the FDA and additional ones are in clinical development for treating cancer. It has been proposed that the efficacy of such antibodies might be enhanced if administered in combination with other approved or experimental cancer therapies, e.g., radiation, surgery, chemotherapeutic agents, targeted therapies, agents that inhibit other signaling pathways that are disregulated in tumors, and other immune enhancing agents.

Pembrolizumab is an anti-PD-1 antibody, which is approved either as monotherapy or combination with certain other agents, in the United States for the treatment of a number of tumor types, including melanoma, non-small cell lung cancer (NSCLC), small cell lung cancer (SCLC), head and neck squamous cell cancer (HNSCC), classical Hodgkin lymphoma (cHL), primary mediastinal large B-cell lymphoma (PMBCL), urothelial carcinoma, microsatellite instability-high cancer, gastric cancer, esophageal cancer, cervical cancer, hepatocellular carcinoma (HCC), Merkel cell carcinoma (MCC), renal cell carcinoma (RCC) and endometrial carcinoma.

Tyrosine kinases are involved in the modulation of growth factor signaling and thus are an important target for cancer therapies. Lenvatinib is an oral receptor tyrosine kinase (RTK) inhibitor that selectively inhibits the kinase activities of vascular endothelial growth factor (VEGF) receptors (VEGFR1 (FLT1), VEGFR2 (KDR), and VEGFR3 (FLT4)), and fibroblast growth factor (FGF) receptors FGFR1, 2, 3 and 4 in addition to other proangiogenic and oncogenic pathway-related RTKs (including the platelet-derived growth factor (PDGF) receptor PDGFRα; KIT; and the RET proto-oncogene (RET)) involved in tumor proliferation. In particular, lenvatinib possesses a new binding mode (Type V) to VEGFR2, as confirmed through X-ray crystal structural analysis, and exhibits rapid and potent inhibition of kinase activity, according to kinetic analysis.

The chemical name of lenvatinib is 4-[3-chloro-4-(cyclopropylaminocarbonyl) aminophenoxy]-7-methoxy-6-quinolinecarboxamide, having the structure:

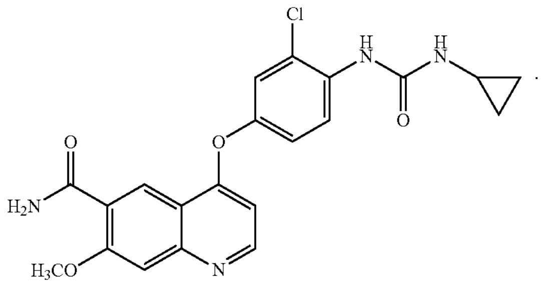 [SMILES: COc1cc2nccc(Oc3ccc(NC(=O)NC4CC4)c(Cl)c3)c2cc1C(N)=O]

Lenvatinib mesylate is approved in the United States at least (a) for the treatment of patients with locally recurrent or metastatic, progressive, radioactive iodine-refractory differentiated thyroid cancer, (b) in combination with everolimus, for the treatment of patients with advanced renal cell carcinoma (RCC) following one prior anti-angiogenic therapy, (c) for the first-line treatment of patients with unresectable hepatocellular carcinoma (HCC) and (d) in combination with pembrolizumab, for the treatment of patients with advanced endometrial carcinoma that is not microsatellite instability-high (MSI-H) or mismatch repair deficient (dMMR), who have disease progression following prior systemic therapy and are not candidates for curative surgery or radiation. Lenvatinib mesylate is under clinical investigation for use as monotherapy or combination therapy with anti-PD-1 antibody for further tumor types, which include bladder cancer, melanoma, head and neck squamous cell cancer, urothelial carcinoma, breast cancer, gastric cancer, ovarian cancer, colorectal cancer (CRC), glioblastoma and biliary tract cancer.

Some cancer cells have been observed to have β-catenin activated by Wnt signal. Inhibitors of the Wnt signal pathway have been studied as anticancer agents; however, none have been put to practical use.

A CBP/β-catenin inhibitor under clinical development as an anticancer agent, is less toxic in human than conventional Wnt inhibitors having other mechanisms (*J. Oncol.* 31, 2013 (suppl; abstr 2501)). As the mechanism thereof, it is considered that, following the inhibition of the binding between CBP (CREB binding protein) and β-catenin, P300 with high similarity to CBP binds β-catenin instead of CBP, and such change suppresses cancer proliferation and induces differentiation (*The EMBO Journal* 2013, 32: 1977-1989).

It has been shown that the main pathway of bile duct cancer can be tumor proliferation by Wnt-β-catenin pathway; a CBP/β-catenin inhibitor, ICG-001, can suppress tumor proliferation (*J. Clin. Invest.* 2015 Mar. 2; 125(3): 1269-85. doi: 10.1172/JCI76452).

Conventional Wnt inhibitors block signals based on mechanisms for inhibiting the production of Wnt ligand, blocking the function of receptor, promoting degradation of β-catenin and the like. Because of such mechanisms, toxicity problems occur in preclinical studies and clinical trials, and the development has mostly been discontinued. The Wnt signaling pathways are highly conserved pathways and are associated with disorders and involve β-catenin. The Wnt/β-catenin pathway is important to normal development. Without being bound by theory, CBP/β-catenin binding is believed to reduce Wnt signaling, whereas p300/β-catenin is believed to activate Wnt signaling.

Furthermore, β-catenin is also known to suppress activation of T cells by suppressing differentiation of T cells (*J. Immunol.* 2011; 186:784-790). Therefore, a CBP/β-catenin inhibitor is considered to promote differentiation of T cells and activation of T cells.

E7386, whose chemical name is (6S,9aS)-N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide, is a potential CBP/β-catenin inhibitor having the structure:

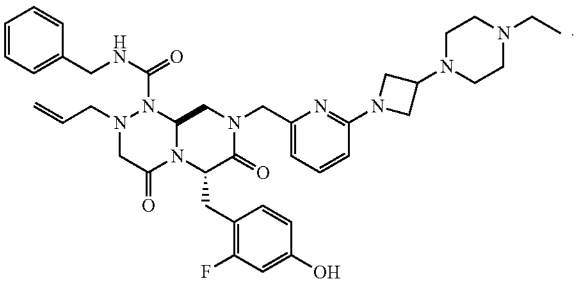

E7386 can exhibit an antitumor effect alone (U.S. Pat. Nos. 10,259,817 and 9,174,998) or in a combination therapy with an anti-PD-1 antibody (U.S. Patent Pub. 2018/0185395) or with lenvatinib (Canadian Patent Pub. 3044658).

In general, tumor therapeutic agents are often not effective for all of the patients when administered individually. Thus, attempts have been made to increase the cure rate of such therapeutic agents by combining them (22).

SUMMARY

As disclosed herein, administration of a combination of (i) a PD-1 antagonist, which is not atezolizumab, (ii) lenvatinib or a pharmaceutically acceptable salt thereof, and (iii) E7386 or a pharmaceutically acceptable salt thereof attains an unexpectedly excellent anti-tumor effect.

A method is provided for treating a cancer in an individual that includes administering to the individual a combination therapy which comprises a PD-1 antagonist, which is not atezolizumab, lenvatinib or a pharmaceutically acceptable salt thereof, and E7386 or a pharmaceutically acceptable salt thereof. In some instances, the individual is a human. The cancer may be a solid tumor, such as a renal cell carcinoma (RCC), a colorectal cancer (CRC), a hepatocellular carcinoma (HCC), a melanoma, a bladder cancer, a breast cancer, a non-small cell lung cancer (NSCLC), an endometrial cancer, a urothelial cancer, and a squamous cell carcinoma of head and neck. The cancer may be an advanced cancer or metastatic cancer.

The PD-1 antagonist of the method may be a monoclonal antibody or an antigen binding fragment thereof. In some instances, the antagonist is an anti-PD-1 antibody. The antagonist may be pembrolizumab or nivolumab.

In some instances, the PD-1 antagonist of the method is pembrolizumab, cemiplimab, or nivolumab, preferably pembrolizumab. Administration of pembrolizumab may occur after the administration of lenvatinib or a pharmaceutically acceptable salt thereof and/or E7386 or a pharmaceutically acceptable salt thereof in some treatment regimens. In some instances, lenvatinib or a pharmaceutically acceptable salt thereof is administered after pembrolizumab and/or E7386 or a pharmaceutically acceptable salt thereof.

A method is provided for treating a human individual diagnosed with a cancer, comprising administering to the individual a combination therapy for at least 24 weeks. The combination therapy includes pembrolizumab, lenvatinib or a pharmaceutically acceptable salt thereof, and E7386 or a pharmaceutically acceptable salt thereof. Lenvatinib or a pharmaceutically acceptable salt thereof may be administered at a daily dose of 24 mg, 20 mg, 18 mg, 12 mg or 8 mg, each as lenvatinib, and pembrolizumab may be administered at a dose of 200 mg Q3W or 400 mg Q6W. E7386 or a pharmaceutically acceptable salt thereof can be administered in a dose ranging from about 0.01 to 1000 mg/kg body weight of the individual per day.

A medicament is provided comprising a PD-1 antagonist for use in combination with lenvatinib or a pharmaceutically acceptable salt thereof and E7386 or a pharmaceutically acceptable salt thereof for treating a cancer.

A medicament is also provided comprising lenvatinib or a pharmaceutically acceptable salt thereof for use in combination with a PD-1 antagonist and E7386 or a pharmaceutically acceptable salt thereof for treating a cancer.

A medicament is also provided comprising E7386 or a pharmaceutically acceptable salt thereof to be used in combination with a PD-1 antagonist and lenvatinib or a pharmaceutically acceptable salt thereof for treating a cancer.

Also provided are uses of a therapeutic combination for treating cancer and the therapeutic combination includes a PD-1 antagonist, lenvatinib or a pharmaceutically acceptable salt thereof, and E7386 or a pharmaceutically acceptable salt thereof.

A use is also provided of a PD-1 antagonist in the manufacture of medicament for treating a cancer in an individual when administered in combination with lenvatinib or a pharmaceutically acceptable salt thereof and E7386 or a pharmaceutically acceptable salt thereof. Also provided is a use of lenvatinib or a pharmaceutically acceptable salt thereof in the manufacture of a medicament for treating a cancer in an individual when administered in combination with a PD-1 antagonist and E7386 or a pharmaceutically acceptable salt thereof. Also provided is a use of E7386 or a pharmaceutically acceptable salt thereof in the manufacture of a medicament for treating a cancer in an individual when administered in combination with a PD-1 antagonist and lenvatinib or a pharmaceutically acceptable salt thereof.

Also provided is a use of a PD-1 antagonist, lenvatinib or a pharmaceutically acceptable salt thereof, and E7386 or a pharmaceutically acceptable salt thereof in the manufacture of medicaments for treating a cancer in an individual. Said medicaments can comprise a kit, and the kit can also comprises a package insert comprising instructions for using the PD-1 antagonist in combination with lenvatinib or a pharmaceutically acceptable salt thereof and E7386 or a pharmaceutically acceptable salt thereof to treat a cancer in an individual.

In all of the treatment methods, medicaments and uses, the PD-1 antagonist inhibits the binding of PD-L1 to PD-1, and preferably also inhibits the binding of PD-L2 to PD-1. In some of the above treatment methods, medicaments and uses, the PD-1 antagonist is a monoclonal antibody, or an antigen binding fragment thereof, which specifically binds to PD-1 or to PD-L1 and blocks the binding of PD-L1 to PD-1. For example, the PD-1 antagonist can be an anti-PD-1 antibody which comprises a heavy chain and a light chain, and wherein the heavy and light chains comprise the amino acid sequences shown in FIG. 6 (SEQ ID NO: 21 and SEQ ID NO: 22). Also provided is a method of treating a tumor that can include the combined use of an anti-PD-1 antibody, lenvatinib or a pharmaceutically acceptable salt thereof, and E7386 or a pharmaceutically acceptable salt thereof.

In some of the combination therapies, treatment methods, medicaments and uses, the individual is a human and the cancer is a solid tumor and in some instances, the solid tumor is a renal cell carcinoma (RCC), a colorectal cancer (CRC), a hepatocellular carcinoma (HCC), a melanoma, a bladder cancer, a urothelial cancer, a breast cancer, a non-small cell lung cancer (NSCLC), an endometrial cancer, and a squamous cell carcinoma of head and neck, or any cancer disclosed herein.

Also, any of the combination therapies, treatment methods, medicaments and uses can be utilized if the cancer tests positive for the expression of one or both of PD-L1 and PD-L2. In still other instances, the cancer has elevated PD-L1 expression.

In some of the combination therapies, treatment methods, medicaments and uses, the individual can be a human, the cancer tests positive for human PD-L1 and is selected from the group consisting of a renal cell carcinoma (RCC), a colorectal cancer (CRC), a hepatocellular carcinoma (HCC), a melanoma, a bladder cancer, a breast cancer, a non-small cell lung cancer (NSCLC), an endometrial cancer, and a squamous cell carcinoma of head and neck. In an embodiment, the bladder cancer is a urothelial cancer.

BRIEF DESCRIPTION OF THE DRAWINGS

FIG. 1 shows amino acid sequences of the light chain and heavy chain CDRs for an exemplary anti-PD-1 monoclonal antibody (SEQ ID NOs: 1-6).

FIG. 2 shows amino acid sequences of the light chain and heavy chain CDRs for another exemplary anti-PD-1 monoclonal antibody (SEQ ID NOs: 7-12).

FIG. 3 shows amino acid sequences of the heavy chain variable region and full length heavy chain for an exemplary anti-PD-1 monoclonal antibody (SEQ ID NO: 13 and SEQ ID NO: 14).

FIG. 4 shows amino acid sequences of alternative light chain variable regions for an exemplary anti-PD-1 monoclonal antibody (SEQ ID NOs: 15-17).

FIGS. 5A and 5B show amino acid sequences of alternative light chains for an exemplary anti-PD-1 monoclonal antibody, with FIG. 5A showing the amino acid sequences for the K09A-L-11 and K09A-L-16 light chains (SEQ ID NOs: 18 and 19, respectively) and FIG. 5B showing the amino acid sequence for the K09A-L-17 light chain (SEQ ID NO: 20).

FIG. 6 shows amino acid sequences of the heavy and light chains for pembrolizumab (SEQ ID NOs: 21 and 22, respectively).

FIG. 7 shows amino acid sequences of the heavy and light chains for nivolumab (SEQ ID NOs: 23 and 24, respectively).

FIGS. 10A to 10C summarizes the mouse cell lines, culture media, animal strains, and conditions employed in the study described in Example 2.

FIG. 11 depicts data obtained in the study described in Example 2. LEN=lenvatinib. PD-1Ab and PD-1=anti-PD-1 antibody. LEN/PD-1=lenvatinib and anti-=PD-1 antibody. E78386=(6S,9aS)-N-benzyl-8-({6-[3-(4-ethylpiperazin-1-yl) azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide E7386/LEN=E7386 and lenvatinib. E7386/LENPD-1=E7386, lenvatinib and anti-PD-1 antibody.

FIG. 12A depicts no treatment data. FIG. 12B depicts data for anti PD-1 antibody (Ab). FIG. 12C depicts data for E7386 at 25 mg/kg. FIG. 12D depicts data for lenvatinib at 10 mg/kg. FIG. 12E depicts data for the combination of E7386 and lenvatinib. FIG. 12F depicts data for the combination of lenvatinib and anti-PD-1 antibody. FIG. 12G depicts data for the combination of E7386, lenvatinib, and anti-PD-1 antibody. In each figure, the cell lines are indicated for the data. The horizontal dotted black lines indicate SD and PR (top and bottom lines, respectively) SD=Stable Disease. PR=Partial Response.

DETAILED DESCRIPTION

Figure 8:
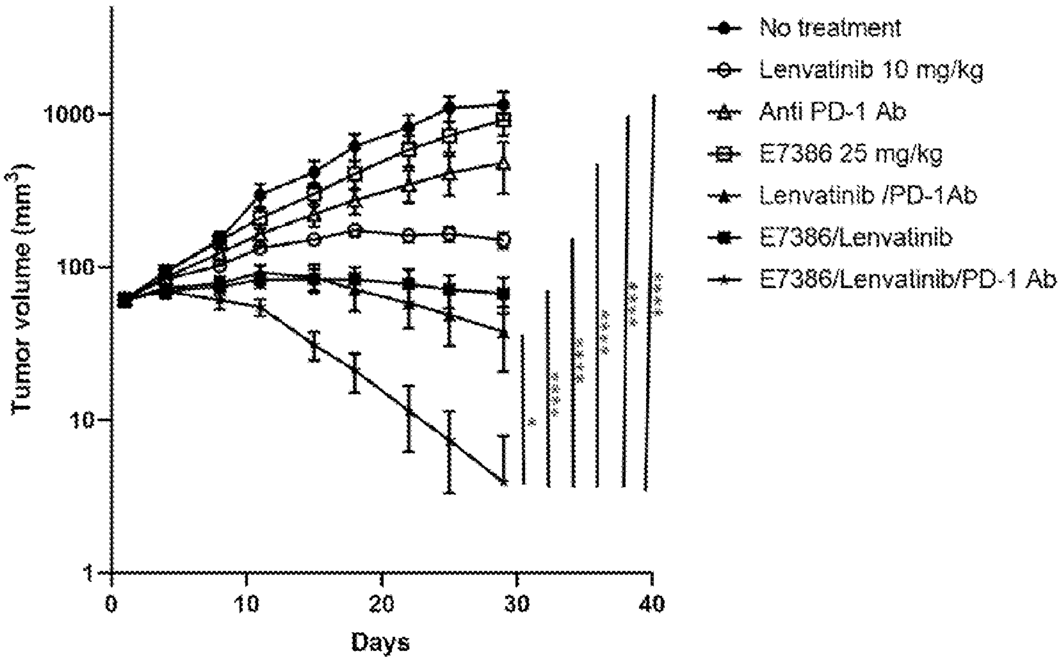
FIG. 8 depicts data for in vivo therapy in mice of a monotherapy of each of the triple drug therapy drug combination, two-drug therapy (lenvatinib+E7386 and pembrolizumab+lenvatinib) and an a triple drug therapy (E7386+lenvatinib+pembrolizumab). The depicts as means±SE. *: $P<0.05$, ****: $P<0.0001$ versus triple combination by repeated measured Dunnet's multiple comparison using Log transformed values. The lenvatinib is lenvatinib mesylate.

Abbreviations. Throughout the detailed description and examples the following abbreviations will be used:

BOR Best overall response
BID One dose twice daily
CBP CREB binding protein
CBR Clinical Benefit Rate
CDR Complementarity determining region
CHO Chinese hamster ovary CR Complete Response
CRC colorectal cancer
DCR Disease Control Rate
DFS Disease free survival
DLT Dose limiting toxicity
DOR Duration of Response
DSDR Durable Stable Disease Rate
FFPE Formalin-fixed, paraffin-embedded
FR Framework region
HCC hepatocellular carcinoma
IgG Immunoglobulin G
IHC Immunohistochemistry or immunohistochemical
irRC Immune related response criteria
IV Intravenous
MCC Merkel cell carcinoma
MTD Maximum tolerated dose
NCBI National Center for Biotechnology Information
NCI National Cancer Institute
NKT Natural Killer T cell
NSCLC Non-small cell lung cancer
ORR Objective response rate
OS Overall survival
PD Progressive disease
PD-1 Programmed Cell Death 1
PD-L1 Programmed Cell Death 1 Ligand 1, also known as B7-H1
PD-L2 Programmed Cell Death 1 Ligand 2, also known as B7-DC
PFS Progression free survival
PR Partial response
Q2W One dose every two weeks
Q3W One dose every three weeks
QD One dose per day
RCC Renal Cell Carcinoma
RECIST Response Evaluation Criteria in Solid Tumors
RTK Receptor tyrosine kinase
SCLC small cell lung cancer
SD Stable disease
VEGF vascular endothelial growth factor
VH Immunoglobulin heavy chain variable region
VK Immunoglobulin kappa light chain variable region Definitions. So that the methods, compositions, and uses may be more readily understood, certain technical and scientific terms are specifically defined below. Unless specifically defined elsewhere in this document, all other technical and scientific terms used herein have the meaning commonly understood by one of ordinary skill in the art.

"About" when used to modify a numerically defined parameter (e.g., the dose of a PD-1 antagonist, 6S,9aS)-N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide (E7386) or a pharmaceutically acceptable salt thereof, or lenvatinib or a pharmaceutically acceptable salt thereof, or the length of treatment time with a combination therapy described herein) means that the parameter may vary by as much as 10% below or above the stated numerical value for that parameter. For example, a dose of about 20 mg may vary between 18 mg and 22 mg.

"Preferably" means a more desirable choice. For example, when used to modify a numerically defined parameter it indicates that the preferred parameter provides an improved result over another value for the parameter. This meaning of "preferably" only applies outside of the United States. For the United States, any sentence using "preferably" should be read as though the term is not present.

As used herein, including the appended claims, the singular forms of words such as "a," "an," and "the," include their corresponding plural references unless the context clearly dictates otherwise.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell. The term "subject" includes any organism, preferably an animal, more preferably a mammal (e.g., rat, mouse, dog, cat, and rabbit) and most preferably a human.

As used herein, the term "antibody" refers to any form of antibody that exhibits the desired biological or binding activity. Thus, it is used in the broadest sense and specifically covers, but is not limited to, monoclonal antibodies (including full length monoclonal antibodies), polyclonal antibodies, multispecific antibodies (e.g., bispecific antibodies), humanized, fully human antibodies, chimeric antibodies, and camelized single domain antibodies. "Parental antibodies" are antibodies obtained by exposure of an immune system to an antigen prior to modification of the antibodies for an intended use, such as humanization of an antibody for use as a human therapeutic.

In general, the basic antibody structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of the heavy chain may define a constant region primarily responsible for effector function. Typically, human light chains are classified as kappa and lambda light chains Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, FUNDAMENTAL IMMUNOLOGY Ch. 7 (Paul, W., ed., 2nd ed. Raven Press, N.Y. (1989).

The variable regions of each light/heavy chain pair form the antibody binding site. Thus, in general, an intact antibody has two binding sites. Except in bifunctional or bispecific antibodies, the two binding sites are, in general, the same.

Typically, the variable domains of both the heavy and light chains comprise three hypervariable regions, also called complementarity determining regions (CDRs), which are located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of SEQUENCES OF PROTEINS OF IMMUNOLOGICAL INTEREST, Kabat, et al.; National Institutes of Health, Bethesda, Md.; 5th ed.; NIH Publ. No. 91-3242 (1991); Kabat (1978) *Adv. Prot. Chem.* 32: 1-75; Kabat, et al., (1977) *J. Biol. Chem.* 252:

6609-6616; Chothia, et al., (1987) *J Mol. Biol.* 196: 901-917 or Chothia, et al., (1989) *Nature* 342: 878-883.

As used herein, the term "hypervariable region" refers to the amino acid residues of an antibody that are responsible for antigen-binding. The hypervariable region comprises amino acid residues from a "complementarity determining region" or "CDR" (i.e. CDRL1, CDRL2 and CDRL3 in the light chain variable domain and CDRH1, CDRH2 and CDRH3 in the heavy chain variable domain). See Kabat et al. (1991) Sequences of Proteins of Immunological Interest, 5th Ed. Public Health Service, National Institutes of Health, Bethesda, Md. (defining the CDR regions of an antibody by sequence); see also Chothia and Lesk (1987) *J. Mol. Biol.* 196: 901-917 (defining the CDR regions of an antibody by structure). As used herein, the term "framework" or "FR" residues refers to those variable domain residues other than the hypervariable region residues defined herein as CDR residues.

"Variable regions" or "V region" as used herein means the segment of IgG chains which is variable in sequence between different antibodies. It extends to Kabat residue 109 in the light chain and 113 in the heavy chain.

As used herein, unless otherwise indicated, "antibody fragment" or "antigen binding fragment" refers to antigen binding fragments of antibodies, i.e. antibody fragments that retain the ability to bind specifically to the antigen bound by the full-length antibody, e.g. fragments that retain one or more CDR regions. Examples of antibody binding fragments include, but are not limited to, Fab, Fab', $F(ab')_2$, and Fv fragments; diabodies; linear antibodies; single-chain antibody molecules, e.g., sc-Fv; nanobodies and multispecific antibodies formed from antibody fragments.

An antibody that "specifically binds to" a specified target protein is an antibody that exhibits preferential binding to that target as compared to other proteins, but this specificity does not require absolute binding specificity. An antibody is considered "specific" for its intended target if its binding is determinative of the presence of the target protein in a sample, e.g. without producing undesired results such as false positives. Antibodies, or binding fragments thereof, will bind to the target protein with an affinity that is at least two fold greater, preferably at least ten times greater, more preferably at least 20-times greater, and most preferably at least 100-times greater than the affinity with non-target proteins. As used herein, an antibody is said to bind specifically to a polypeptide comprising a given amino acid sequence, e.g. the amino acid sequence of a mature human PD-1 or human PD-L1 molecule, if it binds to polypeptides comprising that sequence but does not bind to proteins lacking that sequence.

"Chimeric antibody" refers to an antibody in which a portion of the heavy and/or light chain is identical with or homologous to corresponding sequences in an antibody derived from a particular species (e.g., human) or belonging to a particular antibody class or subclass, while the remainder of the chain(s) is identical with or homologous to corresponding sequences in an antibody derived from another species (e.g., mouse) or belonging to another antibody class or subclass, as well as fragments of such antibodies, so long as they exhibit the desired biological activity.

"Human antibody" refers to an antibody that comprises human immunoglobulin protein sequences only. A human antibody may contain murine carbohydrate chains if produced in a mouse, in a mouse cell, or in a hybridoma derived from a mouse cell. Similarly, "mouse antibody" or "rat antibody" refer to an antibody that comprises only mouse or rat immunoglobulin sequences, respectively.

"Humanized antibody" refers to forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The prefix "hum", "hu" or "h" is added to antibody clone designations when necessary to distinguish humanized antibodies from parental rodent antibodies. The humanized forms of rodent antibodies will generally comprise the same CDR sequences of the parental rodent antibodies, although certain amino acid substitutions may be included to increase affinity, increase stability of the humanized antibody, or for other reasons.

"Isolated antibody" and "isolated antibody fragment" refers to the purification status and in such context means the named molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

"Kabat" as used herein means an immunoglobulin alignment and numbering system pioneered by Elvin A. Kabat ((1991) Sequences of Proteins of Immunological Interest, 5th Ed. Public Health Service, National Institutes of Health, Bethesda, Md.).

"Monoclonal antibody" or "mAb" or "Mab", as used herein, refers to a population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their CDRs, which are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the treatment methods, medicaments, and disclosed uses may be made by the hybridoma method first described by Kohler et al. (1975) *Nature* 256: 495, or may be made by recombinant deoxyribonucleic acid (DNA) methods (see, e.g., U.S. Pat. No. 4,816,567). The "monoclonal antibodies" may also be isolated from phage antibody libraries using the techniques described in Clackson et al. (1991) *Nature* 352: 624-628 and Marks et al. (1991) *J. Mol. Biol.* 222: 581-597, for example. See also Presta (2005) *J. Allergy Clin. Immunol.* 116: 731.

"CDR" or "CDRs" as used herein means complementarity determining region(s) in a immunoglobulin variable region, defined using the Kabat numbering system, unless otherwise indicated.

"Anti-tumor response" when referring to a cancer patient treated with a therapeutic regimen, such as a combination therapy described herein, means at least one positive therapeutic effect, such as for example, reduced number of cancer cells, reduced tumor size, reduced rate of cancer cell infiltration into peripheral organs, reduced rate of tumor metastasis or tumor growth, or progression free survival. Positive therapeutic effects in cancer can be measured in a number of ways (see, W. A. Weber, *J. Null. Med.* 50: 1S-10S (2009); Eisenhauer et al., supra). In some instances, an anti-tumor response to a combination therapy described herein is assessed using RECIST 1.1 criteria (response evaluation criteria in solid tumors), bidimensional irRC (immune related response criteria), or unidimensional irRC. In some instances, an anti-tumor response is any of SD, PR, CR, PFS, or DFS.

"Bidimensional irRC" refers to the set of criteria described in Wolchok J D, et al. "Guidelines for the evaluation of immune therapy activity in solid tumors immune-related response criteria," *Clin Cancer Res.* 15(23): 7412-7420 (2009). These criteria utilize bidimensional tumor measurements of target lesions, which are obtained by multiplying the longest diameter and the longest perpendicular diameter ($cm^2$) of each lesion.

"Biotherapeutic agent" means a biological molecule, such as an antibody or fusion protein, that blocks ligand/receptor signaling in any biological pathway that supports tumor maintenance and/or growth or suppresses the anti-tumor immune response. Classes of biotherapeutic agents include, but are not limited to, antibodies to VEGF, epidermal growth factor receptor (EGFR), Her2/neu, other growth factor receptors, CD20, CD40, CD-40L, CTLA-4, OX-40, 4-1BB, and ICOS.

The terms "cancer," "cancerous," "tumor," or "malignant" refer to or describe the physiological condition in mammals that is typically characterized by unregulated cell growth. Examples of cancer include but are not limited to, renal cell carcinoma (RCC), colorectal cancer (CRC), hepatocellular carcinoma (HCC), melanoma, bladder cancer such as urothelial cancer, breast cancer, non-small cell lung cancer (NSCLC), endometrial cancer, and squamous cell carcinoma of head and neck. Another particular example of cancer includes renal cell carcinoma (RCC). A further particular example of cancer includes clear cell kidney cancer. The cancers can be a primary cancer, but may more likely be advanced in cancer staging including metastatic disease (e.g., lymph or other organ involvement). Cancers that may be treated in accordance with the disclosed treatment methods, medicaments, and disclosed uses include those characterized by elevated expression of one or both of PD-L1 and PD-L2 in tested tissue samples.

"CBR" or "Clinical Benefit Rate" means CR+PR+durable SD.

"Chemotherapeutic agent" is a chemical compound useful in the treatment of a cancer. Classes of chemotherapeutic agents that can be used in combination with the therapeutic combination and its methods and uses described herein include, but are not limited to: alkylating agents, antimetabolites, kinase inhibitors, spindle poison plant alkaloids, cytotoxic/antitumor antibiotics, topoisomerase inhibitors, photosensitizers, anti-estrogens and selective estrogen receptor modulators (SERMs), anti-progesterones, estrogen receptor down-regulators (ERDs), estrogen receptor antagonists, leutinizing hormone-releasing hormone agonists, anti-androgens, aromatase inhibitors, EGFR (epidermal growth factor receptor) inhibitors, VEGF (vascular endothelial growth factor) inhibitors, VEGFR (vascular endothelial growth factor receptor) inhibitors, and anti-sense oligonucleotides that inhibit expression of genes implicated in abnormal cell proliferation or tumor growth. Chemotherapeutic agents useful in the treatment methods disclosed herein include cytostatic and/or cytotoxic agents.

"Chothia" as used herein means an antibody numbering system described in Al-Lazikani et al., *JMB* 273: 927-948 (1997).

"Comprising" or variations such as "comprise", "comprises" or "comprised of" are used throughout the specification and claims in an inclusive sense, i.e., to specify the presence of the stated features but not to preclude the presence or addition of further features that may materially enhance the operation or utility of any of the disclosed treatment methods, medicaments, and disclosed uses, unless the context requires otherwise due to express language or necessary implication.

"Conservatively modified variants" or "conservative substitution" refers to substitutions of amino acids in a protein with other amino acids having similar characteristics (e.g., charge, side-chain size, hydrophobicity/hydrophilicity, backbone conformation and rigidity, etc.), such that the changes can frequently be made without altering the biological activity or other desired property of the protein, such as antigen affinity and/or specificity. Those of skill in this art recognize that, in general, single amino acid substitutions in non-essential regions of a polypeptide do not substantially alter biological activity (see, e.g., Watson et al. (1987) *Molecular Biology of the Gene*, The Benjamin/Cummings Pub. Co., p. 224 (4th Ed.)). In addition, substitutions of structurally or functionally similar amino acids are less likely to disrupt biological activity. Exemplary conservative substitutions are set forth in Table 1 below.

TABLE 1

Exemplary Conservative Amino Acid Substitutions

| Original residue | Conservative substitution |
|---|---|
| Ala (A) | Gly; Ser |
| Arg (R) | Lys; His |
| Asn (N) | Gin; His |
| Asp (D) | Glu; Asn |
| Cys (C) | Ser; Ala |
| Gin (Q) | Asn |
| Glu (E) | Asp;Gin |
| Gly(G) | Ala |
| His (H) | Asn; Gin |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser(S) | Thr |
| Thr (T) | Ser |
| Trp (W) | Tyr; Phe |
| Tyr (Y) | Trp; Phe |
| Val (V) | Ile; Leu |

"Consists essentially of," and variations such as "consist essentially of" or "consisting essentially of,"" as used throughout the specification and claims, indicate the inclusion of any recited elements or group of elements, and the optional inclusion of other elements, of similar or different nature than the recited elements, that do not materially change the basic or novel properties of the specified dosage regimen, method, or composition. As a non-limiting example, a PD-1 antagonist that consists essentially of a recited amino acid sequence may also include one or more amino acids, including substitutions of one or more amino acid residues, which do not materially affect the properties of the binding compound.

"DCR" or "Disease Control Rate" means CR+PR+SD.

"Diagnostic anti-PD-L monoclonal antibody" means a mAb which specifically binds to the mature form of the designated PD-L (PD-L1 or PDL2) that is expressed on the surface of certain mammalian cells. A mature PD-L lacks the presecretory leader sequence, also referred to as leader peptide. The terms "PD-L" and "mature PD-L" are used interchangeably herein, and will be understood to mean the same molecule unless otherwise indicated or readily apparent from the context.

As used herein, a diagnostic anti-human PD-L1 mAb or an anti-hPD-L1 mAb refers to a monoclonal antibody that specifically binds to mature human PD-L1. A mature human PD-L1 molecule consists of amino acids 19-290 of the following sequence:

```
                                  (SEQ ID NO: 25)
MRIFAVFIFMTYWHLLNAFTVTVPKDLYVVEYGSNM

TIECKFPVEKQLDLAALIVYWEMEDKNIIQFVHGE

EDLKVQHSSYRQRARLLKDQLSLGNAALQITDVKL

QDAGVYRCMISYGGADYKRITVKVNAPYNKINQRI

LVVDPVTSEHELTCQAEGYPKAEVIWTSSDHQVLS

GKTTTTNSKREEKLFNVTSTLRINTTTNEIFYCTF

RRLDPEENHTAELVIPELPLAHPPNERTHLVILGA

ILLCLGVALTFIFRLRKGRMMDVKKCGIQDTNSKK

QSDTHLEET.
```

Specific examples of diagnostic anti-human PD-L1 mAbs useful as diagnostic mAbs for IHC detection of PD-L1 expression in FFPE tumor tissue sections are antibody 20C3 and antibody 22C3, which are described in International application PCT/US13/075932, filed 18 Dec. 2013 and published as WO2014/100079 on 26 Jun. 2014. Another anti-human PD-L1 mAb that has been reported to be useful for IHC detection of PD-L1 expression in FFPE tissue sections (Chen, B. J. et al., *Clin. Cancer Res.* 19: 3462-3473 (2013)) is a rabbit anti-human PD-L1 mAb publicly available from Sino Biological, Inc. (Beijing, P.R. China; Catalog number 10084-R015).

"DSDR" or "Durable Stable Disease Rate" means SD for ≥23 weeks.

"Framework region" or "FR" as used herein means the immunoglobulin variable regions excluding the CDR regions.

"Homology" refers to sequence similarity between two polypeptide sequences when they are optimally aligned. When a position in both of the two compared sequences is occupied by the same amino acid monomer subunit, e.g., if a position in a light chain CDR of two different Abs is occupied by alanine, then the two Abs are homologous at that position. The percent of homology is the number of homologous positions shared by the two sequences divided by the total number of positions compared×100. For example, if 8 of 10 of the positions in two sequences are matched or homologous when the sequences are optimally aligned then the two sequences are 80% homologous. Generally, the comparison is made when two sequences are aligned to give maximum percent homology. For example, the comparison can be performed by a Basic Local Alignment Search Tool (BLAST®) algorithm, which is a registered mark of the National Library of Medicine, wherein the parameters of the algorithm are selected to give the largest match between the respective sequences over the entire length of the respective reference sequences.

The following representative references relate to BLAST® algorithms often used for sequence analysis: BLAST ALGORITHMS: Altschul, S. F., et al., (1990) *J. Mol. Biol.* 215: 403-410; Gish, W., et al., (1993) *Nature Genet.* 3: 266-272; Madden, T. L., et al., (1996) *Meth. Enzymol.* 266: 131-141; Altschul, S. F., et al., (1997) *Nucleic Acids Res.* 25:3389-3402; Zhang, J., et al., (1997) *Genome Res.* 7: 649-656; Wootton, J. C., et al., (1993) *Comput. Chem.* 17: 149-163; Hancock, J. M. et al., (1994) *Comput. Appl. Biosci.* 10: 67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in Atlas of Protein Sequence and Structure, (1978) vol. 5, suppl. 3." M. O. Dayhoff (ed.), pp. 353-358, Natl. Biomed. Res. Found., Washington, D.C.; Altschul, S. F., (1991) J. *Mol. Biol.* 219: 555-565; States, D. J., et al., (1991) *Methods* 3: 66-70; Henikoff, S., et al., (1992) *Proc. Natl. Acad. Sci. USA* 89: 10915-10919; Altschul, S. F., et al., (1993) *J. Mol. Evol.* 36: 290-300; ALIGNMENT STATISTICS: Karlin, S., et al., (1990) *Proc. Natl. Acad. Sci. USA* 87: 2264-2268; Karlin, S., et al., (1993) *Proc. Natl. Acad. Sci. USA* 90: 5873-5877; Dembo, A., et al., (1994) *Ann. Prob.* 22: 2022-2039; and Altschul, S. F. "Evaluating the statistical significance of multiple distinct local alignments." in Theoretical and Computational Methods in Genome Research (S. Suhai, ed.), (1997) pp. 1-14, Plenum, New York.

"Non-responder patient", when referring to a specific anti-tumor response to treatment with a combination therapy described herein, means the patient did not exhibit the anti-tumor response.

"ORR" or "objective response rate" refers in some instances to CR+PR, and $ORR_{(week\ 24)}$ refers to CR and PR measured using irRECIST in each patient in a cohort after 24 weeks of treatment with lenvatinib mesylate in combination with pembrolizumab.

"Patient" or "subject" or "individual" refers to any single subject for which therapy is desired or that is participating in a clinical trial, epidemiological study or used as a control, including humans and mammalian veterinary patients such as cattle, horses, dogs, and cats.

PD-1 Antagonists. Anti-PD1 antagonists include the following. A "PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any of the treatment methods, medicaments and disclosed uses in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.:

NP_054862 and NP_079515, respectively. The PD-1 antagonist is not the anti-PD-L1 monoclonal antibody atezolizumab.

PD-1 antagonists useful in the any of the treatment methods, medicaments and disclosed uses include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. The human constant region is selected from the group consisting of IgG1, IgG2, IgG3 and IgG4 constant regions, and preferably the human constant region is an IgG1 or IgG4 constant region. In some instances, the antigen binding fragment is selected from the group consisting of Fab, Fab'-SH, $F(ab')_2$, scFv and Fv fragments.

Any monoclonal antibodies that bind to a PD-1 polypeptide, a PD-1 polypeptide 10 fragment, a PD-1 peptide, or a PD-1 epitope and block the interaction between PD-1 and its ligand PD-L1 or PD-L2 can be used. In some embodiments, the anti-human PD-1 monoclonal antibody binds to a PD-1 polypeptide, a PD-1 polypeptide fragment, a PD-1 peptide, or a PD-1 epitope and blocks the interaction between PD-1 and PD-L1. In other embodiments, the anti-human PD-1 monoclonal antibody binds to a PD-1 polypeptide, a PD-1 polypeptide fragment, a PD-1 peptide, or a PD-1 epitope and blocks the interaction between PD-1 and PD-L2. In yet other embodiments, the anti-human PD-1 monoclonal antibody binds to a PD-1 polypeptide, a PD-1 polypeptide fragment, a PD-1 peptide, or a PD-1 epitope and blocks the interaction between PD-1 and PD-L1 and the interaction between PD-1 and PD-L2.

Any monoclonal antibodies that bind to a PD-L1 polypeptide, a PD-L1 20 polypeptide fragment, a PD-L1 peptide, or a PD-L1 epitope and block the interaction between PD-L1 and PD-1 can also be used.

In certain embodiments, the anti-human PD-1 monoclonal antibody is selected from the group consisting of pembrolizumab, nivolumab, cemiplimab, pidilizumab (U.S. Pat. No. 7,332,582), AMP-514 (MedImmune LLC, Gaithersburg, Md.), PDR001 (U.S. Pat. No. 25 9,683,048), BGB-A317 (U.S. Pat. No. 8,735,553), and MGA012 (MacroGenics, Rockville, Md.).

In one embodiment, the anti-human PD-1 monoclonal antibody is pembrolizumab. In another embodiment, the anti-human PD-1 monoclonal antibody is nivolumab. In another embodiment, the anti-human PD-1 monoclonal antibody is cemiplimab. In yet another embodiment, the anti-human PD-1 monoclonal antibody is pidilizumab. In one embodiment, the anti-human PD-1 monoclonal antibody is AMP-514. In another embodiment, the anti-human PD-1 monoclonal antibody is PDR001. In yet another embodiment, the anti-human PD-1 monoclonal antibody is BGB-A317. In still another embodiment, the anti-human PD-1 monoclonal antibody is MGA012.

Examples of mAbs that bind to human PD-1, and useful in the treatment methods, medicaments and disclosed uses, are described in U.S. Pat. Nos. 7,488,802, 7,521,051, 8,008,449, 8,354,509, and 8,168,757; in International Patent Publications WO2004/004771, WO2004/072286, and WO2004/056875, and in US Pub. No. 2011/0271358. Specific anti-human PD-1 mAbs useful as the PD-1 antagonist in the treatment methods, medicaments and disclosed uses include: pembrolizumab (also known as MK-3475), a humanized IgG4 mAb with the structure described in *WHO Drug Information*, Vol. 27, No. 2, pages 161-162 (2013) and which comprises the heavy and light chain amino acid sequences shown in FIG. 6, nivolumab (BMS-936558), a human IgG4 mAb with the structure described in *WHO Drug Information*, Vol. 27, No. 1, pages 68-69 (2013) and which comprises the heavy and light chain amino acid sequences shown in FIG. 7, pidilizumab, a humanized monoclonal antibody, AMP-224, and AMP-514; the humanized antibodies h409A11, h409A16 and h409A17, which are described in WO2008/156712, and AMP-514, which is being developed by MedImmune.

Examples of mAbs that bind to human PD-L1, and useful in the treatment methods, medicaments and disclosed uses, are described in WO2013/019906, WO2010/077634 A1 and U.S. Pat. No. 8,383,796. Specific anti-human PD-L1 mAbs useful as the PD-1 antagonist in the treatment methods, medicaments and disclosed uses include BMS-936559, cemiplimab, MEDI4736, MSB0010718C and an antibody which comprises the heavy chain and light chain variable regions of SEQ ID NO: 24 and SEQ ID NO: 21, respectively, of WO2013/019906.

Other PD-1 antagonists useful in the any of the treatment methods, medicaments and disclosed uses include an immunoadhesin that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesin molecules that specifically bind to PD-1 are described in WO2010/027827 and WO2011/066342. Specific fusion proteins useful as a PD-1 antagonist in the treatment methods, medicaments and uses described herein include AMP-224 (also known as B7-DCIg), which is a PD-L2-FC fusion protein and binds to human PD-1.

The treatment methods, medicaments and disclosed uses provide for the PD-1 antagonist to be a monoclonal antibody, or antigen binding fragment thereof, which comprises: (a) light chain CDRs SEQ ID NOs: 1, 2 and 3 and heavy chain CDRs SEQ ID NOs: 4, 5 and 6; or (b) light chain CDRs SEQ ID NOs: 7, 8 and 9 and heavy chain CDRs SEQ ID NOs: 10, 11 and 12.

The treatment methods, medicaments and disclosed uses provide for the PD-1 antagonist to be a monoclonal antibody, or antigen binding fragment thereof, which specifically binds to human PD-1 and comprises (a) a heavy chain variable region comprising SEQ ID NO:13 or a variant thereof, and (b) a light chain variable region comprising an amino acid sequence selected from the group consisting of SEQ ID NO: 15 or a variant thereof; SEQ ID NO: 16 or a variant thereof; and SEQ ID NO: 17 or a variant thereof. A variant of a heavy chain variable region sequence is identical to the reference sequence except having up to 17 conservative amino acid substitutions in the framework region (i.e., outside of the CDRs), and preferably has less than ten, nine, eight, seven, six or five conservative amino acid substitutions in the framework region. A variant of a light chain variable region sequence is identical to the reference sequence except having up to five conservative amino acid substitutions in the framework region (i.e., outside of the CDRs), and preferably has less than four, three or two conservative amino acid substitution in the framework region.

The PD-1 antagonist for any of the treatment methods, medicaments and disclosed uses, can be a monoclonal antibody which specifically binds to human PD-1 and comprises (a) a heavy chain comprising SEQ ID NO: 14 and (b) a light chain comprising SEQ ID NO: 18, SEQ ID NO: 19 or SEQ ID NO: 20.

The treatment methods, medicaments and disclosed uses provide for the PD-1 antagonist to be a monoclonal antibody which specifically binds to human PD-1 and comprises (a) a heavy chain comprising SEQ ID NO: 14 and (b) a light chain comprising SEQ ID NO:18.

Table 2 below provides a list of the amino acid sequences of exemplary anti-PD-1 mAbs for use in the treatment methods, medicaments and disclosed uses, and the sequences are shown in FIGS. 1-5B.

TABLE 2

EXEMPLARY ANTI-HUMAN PD-1 MONOCLONAL ANTIBODIES

| | |
|---|---|
| A. Comprises light and heavy chain CDRs of hPD-1.08A in WO2008/156712 | |
| CDRL1 | SEQ ID NO:1 |
| CDRL2 | SEQ ID NO:2 |
| CDRL3 | SEQ ID NO:3 |
| CDRH1 | SEQ ID NO:4 |
| CDRH2 | SEQ ID NO:5 |
| CDRH3 | SEQ ID NO:6 |
| B. Comprises light and heavy chain CDRs of hPD-1.09A in WO2008/156712 | |
| CDRL1 | SEQ ID NO:7 |
| CDRL2 | SEQ ID NO:8 |
| CDRL3 | SEQ ID NO:9 |
| CDRH1 | SEQ ID NO:10 |
| CDRH2 | SEQ ID NO:11 |
| CDRH3 | SEQ ID NO:12 |
| C. Comprises the mature h109A heavy chain variable region and one of the mature K09A light chain variable regions in WO2008/156712 | |
| Heavy chain VR | SEQ ID NO:13 |
| Light chain VR | SEQ ID NO:15 or SEQ ID NO:16 or SEQ ID NO:17 |
| D. Comprises the mature 409 heavy chain and one of the mature K09A light chains in WO2008/156712 | |
| Heavy chain | SEQ ID NO: 14 |
| Light chain | SEQ ID NO: 18 or SEQ ID NO: 19 or SEQ ID NO:20 |

"PD-L1" or "PD-L2" expression as used herein means any detectable level of expression of the designated PD-L protein on the cell surface or of the designated PD-L mRNA within a cell or tissue. PD-L protein expression may be detected with a diagnostic PD-L antibody in an IHC assay of a tumor tissue section or by flow cytometry. Alternatively, PD-L protein expression by tumor cells may be detected by positron emission tomography (PET) imaging, using a binding agent (e.g., antibody fragment, affibody and the like) that specifically binds to the desired PD-L target, e.g., PD-L1 or PD-L2. Techniques for detecting and measuring PD-L mRNA expression include RT-PCR and real-time quantitative RT-PCR.

Several approaches have been described for quantifying PD-L1 protein expression in IHC assays of tumor tissue sections. See, e.g., Thompson, R. H., et al., *PNAS* 101 (49): 17174-17179 (2004); Thompson, R. H. et al., *Cancer Res.* 66: 3381-3385 (2006); Gadiot, J., et al., *Cancer* 117: 2192-2201 (2011); Taube, J. M. et al., *Sci Transl Med* 4: 127-37 (2012); and Toplian, S. L. et al., *New Eng. J Med.* 366(26): 2443-2454 (2012).

One approach employs a simple binary end-point of positive or negative for PD-L1 expression, with a positive result defined in terms of the percentage of tumor cells that exhibit histologic evidence of cell-surface membrane staining. A tumor tissue section is counted as positive for PD-L1 expression is at least 1%, and preferably 5% of total tumor cells.

In another approach, PD-L1 expression in the tumor tissue section is quantified in the tumor cells as well as in infiltrating immune cells, which predominantly comprise lymphocytes. The percentage of tumor cells and infiltrating immune cells that exhibit membrane staining are separately quantified as <5%, 5 to 9%, and then in 10% increments up to 100%. For tumor cells, PD-L1 expression is counted as negative if the score is <5% score and positive if the score is ≥5%. PD-L1 expression in the immune infiltrate is reported as a semi-quantitative measurement called the adjusted inflammation score (AIS), which is determined by multiplying the percent of membrane staining cells by the intensity of the infiltrate, which is graded as none (0), mild (score of 1, rare lymphocytes), moderate (score of 2, focal infiltration of tumor by lymphohistiocytic aggregates), or severe (score of 3, diffuse infiltration). A tumor tissue section is counted as positive for PD-L1 expression by immune infiltrates if the AIS is ≥5.

The level of PD-L mRNA expression may be compared to the mRNA expression levels of one or more reference genes that are frequently used in quantitative RT-PCR, such as ubiquitin C.

In some instances, a level of PD-L1 expression (protein and/or mRNA) by malignant cells and/or by infiltrating immune cells within a tumor is determined to be "overexpressed" or "elevated" based on comparison with the level of PD-L1 expression (protein and/or mRNA) by an appropriate control. For example, a control PD-L1 protein or mRNA expression level may be the level quantified in nonmalignant cells of the same type or in a section from a matched normal tissue (i.e. non-malignant tissue). PD-L1 expression in a tumor sample is preferably determined to be elevated if PD-L1 protein (and/or PD-L1 mRNA) in the sample is at least 10%, 20%, or 30% greater than in the control.

A "pembrolizumab biosimilar" means a biological product manufactured by an entity other than Merck & Co., Inc. d.b.a. Merck Sharp and Dohme (MSD) and which is approved by a regulatory agency in any country for marketing as a pembrolizumab biosimilar. A pembrolizumab biosimilar may include as the drug substance a pembrolizumab variant or an antibody with the same amino acid sequence as pembrolizumab.

As used herein, a "pembrolizumab variant" means a monoclonal antibody which comprises heavy chain and light chain sequences that are identical to those in pembrolizumab, except for having three, two or one conservative amino acid substitutions at positions that are located outside of the light chain CDRs and six, five, four, three, two or one conservative amino acid substitutions that are located outside of the heavy chain CDRs, e.g, the variant positions are located in the FR regions and/or the constant region. In other words, pembrolizumab and a pembrolizumab variant comprise identical CDR sequences, but differ from each other due to having a conservative amino acid substitution at no more than three or six other positions in their full length light and heavy chain sequences, respectively. A pembrolizumab variant is substantially the same as pembrolizumab with respect to the following properties: binding affinity to PD-1 and ability to block the binding of each of PD-L1 and PD-L2 to PD-1.

Patient/Cancer/Response Definitions. "RECIST 1.1 Response Criteria" as used herein means the definitions set forth in Eisenhauer et al., E. A. et al., *Eur. J. Cancer* 45:

228-247 (2009) for target lesions or nontarget lesions, as appropriate based on the context in which response is being measured.

"Responder patient" when referring to a specific anti-tumor response to treatment with a combination therapy described herein, means the patient exhibited the anti-tumor response.

"Sustained response" means a sustained therapeutic effect after cessation of treatment with a therapeutic agent, or a combination therapy described herein. In some instances, the sustained response has a duration that is at least the same as the treatment duration, or at least 1.5, 2.0, 2.5 or 3 times longer than the treatment duration.

"Tissue Section" refers to a single part or piece of a tissue sample, e.g., a thin slice of tissue cut from a sample of a normal tissue or of a tumor.

"Treat" or "treating" a cancer as used herein means to administer a combination therapy of a PD-1 antagonist, lenvatinib or a pharmaceutically acceptable salt thereof, and E7386 or a pharmaceutically acceptable salt thereof to a subject having a cancer, or diagnosed with a cancer, to achieve at least one positive therapeutic effect, such as for example, reduced number of cancer cells, reduced tumor size, reduced rate of cancer cell infiltration into peripheral organs, or reduced rate of tumor metastasis or tumor growth. Positive therapeutic effects in cancer can be measured in a number of ways (see, W. A. Weber, *J. Nucl. Med.* 50:1S-10S (2009)). For example, with respect to tumor growth inhibition, according to NCI standards, a T/C≤42% is the minimum level of anti-tumor activity. A T/C<10% is considered a high anti-tumor activity level, with T/C (%)=Median tumor volume of the treated/Median tumor volume of the control×100. In some instances, response to a combination therapy described herein is assessed using RECIST 1.1 criteria or irRC (bidimensional or unidimensional) and the treatment achieved by a combination of lenvatinib or a pharmaceutically acceptable salt thereof, (6S,9aS)-N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide (E7386) or a pharmaceutically acceptable salt thereof, and a PD-1 antagonist is any of PR, CR, OR, PFS, DFS and OS. PFS, also referred to as "Time to Tumor Progression" indicates the length of time during and after treatment that the cancer does not grow, and includes the amount of time patients have experienced a CR or PR, as well as the amount of time patients have experienced SD. DFS refers to the length of time during and after treatment that the patient remains free of disease. OS refers to a prolongation in life expectancy as compared to naive or untreated individuals or patients. In some instances, response to a combination of a lenvatinib or a pharmaceutically acceptable salt thereof, 6S,9aS)-N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide (E7386) or a pharmaceutically acceptable salt thereof, and a PD-1 antagonist is any of PR, CR, PFS, DFS, OR and OS that is assessed using RECIST 1.1 response criteria. The treatment regimen for the disclosed combination that is effective to treat a cancer patient may vary according to factors such as the disease state, age, and weight of the patient, and the ability of the therapy to elicit an anti-cancer response in the subject. The treatment methods, medicaments, and disclosed uses may not be effective in achieving a positive therapeutic effect in every subject, they should do so in a statistically significant number of subjects as determined by any statistical test known in the art such as the Student's t-test, the $chi^2$-test, the U-test according to Mann and Whitney, the Kruskal-Wallis test (H-test), Jonckheere-Terpstra-test and the Wilcoxon-test.

The terms "treatment regimen", "dosing protocol" and "dosing regimen" are used interchangeably to refer to the dose and timing of administration of each therapeutic agent in a combination of a lenvatinib or a pharmaceutically acceptable salt thereof, (6S,9aS)-N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide (E7386) or a pharmaceutically acceptable salt thereof, and a PD-1 antagonist.

"Tumor" as it applies to a subject diagnosed with, or suspected of having, a cancer refers to a malignant or potentially malignant neoplasm or tissue mass of any size, and includes primary tumors and secondary neoplasms. A solid tumor is an abnormal growth or mass of tissue that usually does not contain cysts or liquid areas. Different types of solid tumors are named for the type of cells that form them. Examples of solid tumors are sarcomas, carcinomas, and lymphomas.

"Tumor burden" also referred to as "tumor load", refers to the total amount of tumor material distributed throughout the body. Tumor burden refers to the total number of cancer cells or the total size of tumor(s), throughout the body, including lymph nodes and bone narrow. Tumor burden can be determined by a variety of methods known in the art, such as, e.g. by measuring the dimensions of tumor(s) upon removal from the subject, e.g., using calipers, or while in the body using imaging techniques, e.g., ultrasound, bone scan, computed tomography (CT) or magnetic resonance imaging (MRI) scans.

The term "tumor size" refers to the total size of the tumor which can be measured as the length and width of a tumor. Tumor size may be determined by a variety of methods known in the art, such as, e.g. by measuring the dimensions of tumor(s) upon removal from the subject, e.g., using calipers, or while in the body using imaging techniques, e.g., bone scan, ultrasound, CT or MRI scans.

"Unidimensional irRC refers to the set of criteria described in Nishino M, Giobbie-Hurder A, Gargano M, Suda M, Ramaiya N H, Hodi F S. "Developing a Common Language for Tumor Response to Immunotherapy Immune-related Response Criteria using Unidimensional measurements," *Clin. Cancer Res.* 2013, 19(14): 3936-3943). These criteria utilize the longest diameter (cm) of each lesion.

By a "multi-RTK inhibitor" means a small molecule compound that inhibits the receptor tyrokine kinase (RTK) activities of at least each of the following RTKs: (i) VEGFR2, and (ii) at least one FGFR selected from the group consisting of FGFR1, 2, 3 and 4. An exemplary multi-RTK inhibitor is lenvatinib or a pharmaceutically acceptable salt thereof.

β-catenin functions as a mediator of Wnt signal transduction, binds to a transcription factor Tcf/Lef (T cell factor/Lymphocyte enhancing factor), promotes expression of various genes (cyclin D1, c-Myc etc.) involved in Wnt signal transduction, and controls proliferation and differentiation of cells (He et al., 1998 *Science* 281: 1509-1512; Kolligs et al., *Mol. Cell. Biol.* 19: 5696-5706, 1999; Crawford et al., *Oncogene* 18: 2883-2891, 1999; Shtutman el al., *Proc. Natl. Acad. Sci. USA,* 11: 5522-5527, 1999; Tetsu and McCormick, 1999 *Nature,* 398: 422-426).

CBP (cyclic AMP response element binding protein (CREB) binding protein) directly interacts with β-catenin in the CREB binding domain, and promotes transcription activation of Tcf/Lef (Ken-Ichi Takemaru and Randall T. Moon, 2000, *J. Cell. Biol.* 149(2): 249-254). A CBP/β-catenin inhibitor is not particularly limited as long as it inhibits interaction between CBP and catenin, particularly β-catenin, and an embodiment in which binding of β-catenin and CBP is inhibited, as a result of which gene expression by β-catenin complex is suppressed is preferable.

Inhibition of CBP/β-catenin can be measured by a binding assay (radiobinding assay etc.) known per se, a reporter assay method, and other in vitro and in vivo assays the like. Inhibition can be confirmed by measuring gene expression of Wnt signal transduction by the reporter assay method described in WO 2009/148192.

The CBP/β-catenin inhibitor of the present invention is not particularly limited as long as it is as defined above. It is preferably an α-helix mimetic compound having a CBP/β-catenin inhibitory activity, and examples thereof include α-helix mimetic compounds, pharmaceutically acceptable salts thereof and the like as described in WO 2003/031448, WO 2004/093828, WO 2005/116032, WO 2009/148192, WO 2010/044485, WO 2010/128685, WO 2012/115286, and the like. An exemplary CBP/β-catenin inhibitor includes (6S,9aS)-N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide (E7386).

Each of the PD-1 antagonist, lenvatinib and E7386 in the combination therapy disclosed herein may be administered either alone or in a medicament/formulation (also referred to herein as a pharmaceutical composition) which comprises the therapeutic agent and one or more pharmaceutically acceptable carriers, excipients and diluents, according to standard pharmaceutical practice. Each therapeutic agent may be prepared by formulating lenvatinib or its pharmaceutically acceptable salt, an anti-PD-1 antibody, and/or a E7386 or its pharmaceutically acceptable salt, may be administered either at the same time or separately. Further, the formulations may be placed in a single package, to provide the so called kit formulation.

Lenvatinib or a pharmaceutically acceptable salt can be produced by the method described in Reference 17. Examples of the pharmaceutically acceptable salt include salts with inorganic acids, salts with organic acids, salts with inorganic bases, salts with organic bases, and salts with acidic or basic amino acids. Preferred examples of the salts with inorganic acids include salts with hydrochloric acid, hydrobromic acid, sulfuric acid, nitric acid, phosphoric acid and the like. Preferred examples of the salts with organic acids include salts with acetic acid, succinic acid, fumaric acid, maleic acid, tartaric acid, citric acid, lactic acid, stearic acid, benzoic acid, methanesulfonic acid, ethanesulfonic acid, p-toluenesulfonic acid and the like. Preferred examples of the salts with inorganic bases include alkaline metal salts such as a sodium salt and a potassium salt; alkaline earth metal salts such as a calcium salt and a magnesium salt; an aluminum salt; and an ammonium salt. Preferred examples of the salts with organic bases include salts with diethylamine, diethanolamine, meglumine, N,N-dibenzylethylenediamine and the like. Preferred examples of the salts with acidic amino acids include salts with aspartic acid, glutamic acid and the like. Preferred examples of the salts with basic amino acids include salts with arginine, lysine, ornithine and the like. More preferred pharmaceutically acceptable salts are salts with organic acids and especially preferred pharmaceutically acceptable salts are salts with methanesulfonic acid.

The PD-1 antagonist, lenvatinib or its pharmaceutically acceptable salt and E7386 or a pharmaceutically acceptable salt thereof—in a combination therapy disclosed herein may be administered simultaneously (i.e., in the same medicament), concurrently (i.e., in separate medicaments administered one right after the other in any order) or sequentially in any order. Sequential administration is particularly useful when the therapeutic agents in the combination therapy are in different dosage forms (one agent is a tablet or capsule and another agent is a sterile liquid) and/or are administered on different dosing schedules, e.g., a chemotherapeutic that is administered at least daily and a biotherapeutic that is administered less frequently, such as once weekly, once every two weeks, or once every three weeks.

In some instances, the lenvatinib or its pharmaceutically acceptable salt is administered before administration of the PD-1 antagonist and/or the CBP/β-catenin inhibitor, while in other instances, the multi-RTK inhibitor is administered after administration of the PD-1 antagonist and/or the E7386 or a pharmaceutically acceptable salt thereof.

In some instances, at least one of the therapeutic agents in the combination therapy is administered using the same dosage regimen (dose, frequency and duration of treatment) that is typically employed when the agent is used as monotherapy for treating the same cancer. In other instances, the patient receives a lower total amount of at least one of the therapeutic agents in the combination therapy than when the agent is used as monotherapy, e.g., smaller doses, less frequent doses, and/or shorter treatment duration.

Each small molecule therapeutic agent in a combination therapy disclosed herein can be administered orally in the form of a solid formulation such as a tablet, granule, fine granule, powder or capsule, or in the form of a liquid, jelly, syrup, or the like. Each small molecule therapeutic agent in a combination therapy disclosed herein may be administered parenterally, including the intravenous, intramuscular, intraperitoneal, subcutaneous, rectal, topical, and transdermal routes of administration.

A combination therapy disclosed herein may be used prior to or following surgery to remove a tumor and may be used prior to, during or after radiation therapy.

In some instances, a combination therapy disclosed herein is administered to a patient who has not been previously treated with a biotherapeutic or chemotherapeutic agent, i.e., is treatment-naïve. In other instances, the combination therapy is administered to a patient who failed to achieve a sustained response after prior therapy with a biotherapeutic or chemotherapeutic agent, i.e., is treatment-experienced.

A combination therapy disclosed herein is typically used to treat a tumor that is large enough to be found by palpation or by imaging techniques well known in the art, such as magnetic resonance imaging (MRI), ultrasound, or computerized axial tomography (CAT) scan.

A combination therapy disclosed herein is preferably administered to a human patient who has a cancer that tests positive for PD-L1 expression. PD-L1 expression is detected preferably using a diagnostic anti-human PD-L1 antibody, or antigen binding fragment thereof, in an IHC assay on an FFPE or frozen tissue section of a tumor sample removed from the patient. Typically, the patient's physician would order a diagnostic test to determine PD-L1 expression in a tumor tissue sample removed from the patient prior to initiation of treatment with the PD-1 antagonist, the E7386 or a pharmaceutically acceptable salt thereof, and lenvatinib or its pharmaceutically acceptable salt, but it is envisioned that the physician could order the first or subsequent diagnostic tests at any time after initiation of treatment, such as for example after completion of a treatment cycle.

Selecting a dosage regimen (also referred to herein as an administration regimen) for a combination therapy disclosed herein depends on several factors, including the serum or tissue turnover rate of the entity, the level of symptoms, the immunogenicity of the entity, and the accessibility of the target cells, tissue or organ in the individual being treated. Preferably, a dosage regimen maximizes the amount of each therapeutic agent delivered to the patient consistent with an acceptable level of side effects. Accordingly, the dose amount and dosing frequency of each biotherapeutic and chemotherapeutic agent in the combination depends in part on the particular therapeutic agent, the severity of the cancer being treated, and patient characteristics. Guidance in selecting appropriate doses of antibodies, cytokines, and small molecules are available. See, e.g., Wawrzynczak (1996) Antibody Therapy, Bios Scientific Pub. Ltd, Oxfordshire, UK; Kresina (ed.) (1991) Monoclonal Antibodies, Cytokines and Arthritis, Marcel Dekker, New York, N.Y.; Bach (ed.) (1993) Monoclonal Antibodies and Peptide Therapy in Autoimmune Diseases, Marcel Dekker, New York, N.Y.; Baert et al. (2003) *New Engl. J. Med.* 348: 601-608; Milgrom et al. (1999) *New Engl. J. Med.* 341: 1966-1973; Slamon et al. (2001) *New Engl. J. Med.* 344: 783-792; Beniaminovitz et al. (2000) *New Engl. J. Med.* 342: 613-619; Ghosh et al. (2003) *New Engl. J. Med.* 348: 24-32; Lipsky et al. (2000) *New Engl. J. Med.* 343: 1594-1602; Physicians' Desk Reference 2003 (Physicians' Desk Reference, 57th Ed.); Medical Economics Company; ISBN: 1563634457; 57th edition (November 2002). Determination of the appropriate dosage regimen may be made by the clinician, e.g., using parameters or factors known or suspected in the art to affect treatment or predicted to affect treatment, and will depend, for example, the patient's clinical history (e.g., previous therapy), the type and stage of the cancer to be treated and biomarkers of response to one or more of the therapeutic agents in the combination therapy.

Biotherapeutic agents in a combination therapy disclosed herein (i.e., the PD-1 antagonist, lenvatinib or its pharmaceutically acceptable salt, and E7386 or its pharmaceutically acceptable salt) may be administered by continuous infusion, or by doses at intervals of, e.g., daily, every other day, three times per week, or one time each week, two weeks, three weeks, monthly, bimonthly, etc. A total weekly dose is generally at least 0.05 μg/kg, 0.2 μg/kg, 0.5 μg/kg, 1 μg/kg, 10 μg/kg, 100 μg/kg, 0.2 mg/kg, 1.0 mg/kg, 2.0 mg/kg, 10 mg/kg, 25 mg/kg, 50 mg/kg body weight or more. See, e.g., Yang et al. (2003) *New Engl. J. Med.* 349: 427-434; Herold et al. (2002) *New Engl. J. Med.* 346: 1692-1698; Liu et al. (1999) *J. Neurol. Neurosurg. Psych.* 67: 451-456; Portielji et al. (2003) *Cancer Immunol. Immunother.* 52: 133-144. Cemiplimab-rwlc (LIBTAYO®) is another PD-1 antagonist. It can be administered in intravenously wherein 350 mg is administered over 30 minutes once every 3 weeks (Q3W).

The dose of lenvatinib or pharmaceutically acceptable salt thereof may be appropriately selected depending on the degrees of symptoms, age, sex, and body weight of the patient, difference in sensitivity, route, time of administration and interval of administration, type of pharmaceutical formulation, and/or the like. Typically, in cases where oral administration is carried out for an adult (60 kg body weight), the dose is 1 to 600 mg, preferably 5 to 400 mg, more preferably 5 to 200 mg per day. The dose may be administered at one time or divided into smaller doses provided 2 to 3 times per day.

In some instances that employ an anti-human PD-1 mAb as the PD-1 antagonist in the combination therapy, the dosing regimen will comprise administering the anti-human PD-1 mAb at a dose of 1, 2, 3, 5 or 10 mg/kg at intervals of about 14 days (±2 days) or about 21 days (±2 days) or about 30 days (±2 days) throughout the course of treatment. The dosage of an anti-PD-1 antibody can be appropriately selected in the same manner as above. Typically, in cases where intravenous administration is carried out for an adult (60 kg body weight), the dose can be 2 mg/kg on a schedule of once every 3 weeks on a 6-week cycle (a total of 2 doses). The antibody can be administered for 1 to 10 cycles at an appropriate interval.

In other instances that employ an anti-human PD-1 mAb as the PD-1 antagonist in the combination therapy, the dosing regimen will comprise administering the anti-human PD-1 mAb at a dose of from about 0.005 mg/kg to about 10 mg/kg, with intra-patient dose escalation. The interval between doses can be progressively shortened, e.g., about 30 days (±2 days) between the first and second dose, about 14 days (±2 days) between the second and third doses. In certain embodiments, the dosing interval will be about 14 days (±2 days), for doses subsequent to the second dose.

In specific instances, a subject can be administered an intravenous (IV) infusion of a medicament comprising any of the PD-1 antagonists described herein.

The PD-1 antagonist in the combination therapy is preferably nivolumab in some instances, which is administered intravenously at a dose selected from the group consisting of: 1 mg/kg Q2W, 2 mg/kg Q2W, 3 mg/kg Q2W, 5 mg/kg Q2W, 10 mg Q2W, 1 mg/kg Q3W, 2 mg/kg Q3W, 3 mg/kg Q3W, 5 mg/kg Q3W, and 10 mg Q3W. The PD-1 antagonist can also be cemiplimab-rwlc administered intravenously at a dose of 350 mg Q3W.

The PD-1 antagonist in the combination therapy preferably is pembrolizumab, a pembrolizumab variant or a pembrolizumab biosimilar in some instances, which is administered in a liquid medicament at a dose selected from the group consisting of 1 mg/kg Q2W, 2 mg/kg Q2W, 3 mg/kg Q2W, 5 mg/kg Q2W, 10 mg Q2W, 1 mg/kg Q3W, 2 mg/kg Q3W, 3 mg/kg Q3W, 5 mg/kg Q3W, 10 mg Q3W and flat-dose equivalents of any of these doses, i.e., such as 200 mg Q3W and 400 mg Q6W. In some instances, pembrolizumab is provided as a liquid medicament which comprises 25 mg/ml pembrolizumab, 7% (w/v) sucrose, 0.02% (w/v) polysorbate 80 in 10 mM histidine buffer pH 5.5.

In some instances, the selected dose of pembrolizumab is administered by IV infusion over a time period of between 25 and 40 minutes, or about 30 minutes.

The optimal dose for pembrolizumab in combination with lenvatinib or a pharmaceutically acceptable salt thereof (e.g., lenvatinib mesylate) and a CBP/β-catenin inhibitor (e.g., E7386) may be identified by dose escalation or dose de-escalation of one or both of these agents. In some instances, the combination therapy comprises a 21 day treatment cycle in which pembrolizumab is administered at 200 mg Q3W by IV (or 400 mg Q6W by IV), a CBP/catenin inhibitor, the lenvatinib mesylate is administered at (a) 24 mg per day orally, (b) 20 mg per day orally or (c) 14 mg per day orally, each as lenvatinib.

A patient can be treated first with a daily amount of a CBP/β-catenin inhibitor, 200 mg of pembrolizumab Q3W by IV (or 400 mg Q6W by IV) and 24 mg (as lenvatinib) of lenvatinib mesylate per day orally until at least one DLT is observed and then the dosage of lenvatinib mesylate can be reduced to 20 or 14 mg (each as lenvatinib) per day, while the pembrolizumab dose can be continued at 200 mg of pembrolizumab Q3W (or 400 mg Q6W by IV) and the CBP/β-catenin inhibitor can be continued at the same daily dosage or reduced.

As an example dosing regimen, lenvatinib or a pharmaceutically acceptable salt thereof can be administered with water orally once a day, with or without food, in 21 day cycles at approximately the same time each day. Lenvatinib or a pharmaceutically acceptable salt thereof can be provided as 4 mg and 10 mg (each as lenvatinib) capsules. On Day one (D1) of each cycle, lenvatinib or a pharmaceutically acceptable salt thereof can be administered approximately within 1 hour after completion of pembrolizumab administration and/or E7386 or its pharmaceutically acceptable salt-administration. Pembrolizumab may be provided as a sterile, preservative-free, white to off-white lyophilized powder in single-use vials. Each vial can be reconstituted and diluted for intravenous infusion. Each 2 mL of reconstituted solution may contain approximately 50 mg of pembrolizumab. In some instances, pembrolizumab may be provided as a sterile, preservative-free, clear to slightly opalescent, colorless to slightly yellow solution that requires dilution for intravenous infusion. Each vial may contain 100 mg of pembrolizumab in 4 mL of solution. Each 1 mL of solution may contain 25 mg of pembrolizumab. Pembrolizumab may be administered as a dose of 200 mg as a 30-minute intravenous infusion, Q3W (25 minutes to 40 minutes, for example).

In cases where an oral solid formulation is prepared, a pharmaceutically acceptable vehicle, and, as required, a binder, disintegrator, lubricant, coloring agent, flavoring agent and/or the like may be added to the principal component, that is, a compound or pharmaceutically acceptable salt thereof represented by Formula (I), a CBP/β-catenin inhibitor, and/or an anti-PD-1 antibody, to prepare, thereafter, a tablet, granule, fine granule, powder, capsule or the like according to a conventional method. Examples of the vehicle include lactose, corn starch, white soft sugar, glucose, sorbitol, crystalline cellulose and silicon dioxide. Examples of the binder include polyvinyl alcohol, ethylcellulose, methylcellulose, gum arabic, hydroxypropylcellulose and hydroxypropylmethylcellulose. Examples of the lubricant include magnesium stearate, talc, and silica. Examples of the coloring agents include titanium oxide, iron sesquioxide, yellow iron sesquioxide, cochineal, carmine, and riboflavin. Examples of the flavoring agents include cocoa powder, ascorbic acid, tartaric acid, peppermint oil, borneol, and cinnamon powder. These tablets and granules may be coated as may be required.

In some instances, the patient is treated with the combination therapy for at least 24 weeks, e.g., eight 3-week cycles. In some instances, treatment with the combination therapy continues until the patient exhibits evidence of PD or a CR.

In some instances, the patient selected for treatment with the combination therapy disclosed herein if the patient has been diagnosed with a renal cell carcinoma (RCC), a colorectal cancer (CRC), a hepatocellular carcinoma (HCC), a melanoma, a bladder cancer, a urothelial cancer, a breast cancer, a non-small cell lung cancer (NSCLC), an endometrial cancer, or a squamous cell carcinoma of head and neck.

A "therapeutic drug" or "combination therapy for a cancer comprises an immune checkpoint inhibitor (e.g., an anti-PD-1 antibody), lenvatinib or a pharmaceutically acceptable salt thereof, and E7386 or a pharmaceutically acceptable salt thereof. The drug may be formulated such that each of the 3 drugs is separate and administered separately or in a combination of two of the three drugs, or altogether by a method appropriate for desired administration, for example, oral, transnasal, mucous membrane, rectal, vaginal, topical, intravenously, intraperitoneal, intradermal, subcutaneous, and intramuscular administration and the like.

Determination of the dose and so the timing of the administration of a therapeutically effective amount of a combination therapy for cancer containing a combination of an immune checkpoint inhibitor, lenvatinib or a pharmaceutically acceptable salt thereof, and E7386 or a pharmaceutically acceptable salt thereof is sufficiently within the knowledge of those of ordinary skill in the art. For example, the initial effective amount can be assumed from the cell culture or other in vitro assay. The dose can be set to create a circulation concentration or tissue concentration, such as $IC_{50}$ concentration and the like, determined by cell culture assay and/or in an animal model.

An administration method is selected relying on the condition under treatment and the therapeutic drug. An immune checkpoint inhibitor, lenvatinib or a pharmaceutically acceptable salt thereof, and E7386 or a pharmaceutically acceptable salt thereof can be administered by various methods. For example, one or more of the components can be administered to a subject via any of the following routes: subcutaneous, intravenous, intraperitoneal, intramuscular and systemic administrations and, in some cases, direct injection into a particular organ or tumor and the like. An immune checkpoint inhibitor, lenvatinib or a pharmaceutically acceptable salt thereof, and E7386 or a pharmaceutically acceptable salt thereof can be administered through a single pathway, or simultaneous several pathways at the same time or sequentially as described herein.

E7386 or a pharmaceutically acceptable salt thereof may be administered once per day, twice per day, several times per day, or further, plural times per day, depending on, among other things, the treatment indication and the judgment of the prescribing physician.

The amounts of an immune checkpoint inhibitor, lenvatinib or a pharmaceutically acceptable salt thereof, and E7386 or a pharmaceutically acceptable salt thereof necessary for affording a treatment effect can be empirically determined according to conventional procedures for a particular object. Generally, cells are given in a pharmacologically effective dose when administered for the object of treatment. The "pharmacologically effective amount" or "pharmacologically effective dose" refers to an amount sufficient for producing a desired physiological effect or capable of achieving a desired result, such as reducing or removing one or more symptoms or indications of a disorder or disease and the like, to treat a particular disorder or disease state.

The combination therapy can be a combination of an immune checkpoint inhibitor, lenvatinib or a pharmaceutically acceptable salt thereof, and E7386 or a pharmaceutically acceptable salt thereof that can be further combined with other cancer treatments, for example, surgical resection, radiation therapy, chemotherapy, immunotherapy, and supporting therapy (e.g., analgesic, diuretic, antidiuretic, antiviral drug, antibiotic, nutritional supplement, anemia treatment, blood coagulation treatment, bone treatment, and psychopathological and psychological treatments) and the like.

These and other aspects disclosed herein, including the exemplary specific treatment methods, medicaments, and uses listed below, will be apparent from the teachings contained herein.

SPECIFIC TREATMENT METHODS, MEDICAMENTS, AND USES

[1]. A method for treating a cancer in a human subject comprising administering to the individual a combination therapy which comprises:

(i) an antagonist of a Programmed Death 1 protein (PD-1);

(ii) lenvatinib having the structure:

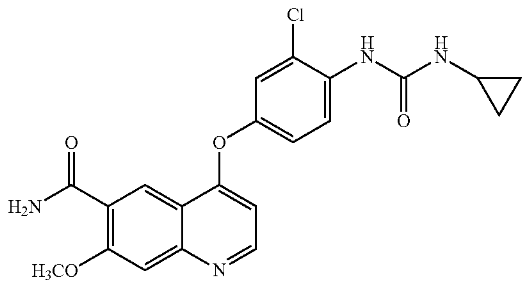 [SMILES: COc1cc2nccc(Oc3ccc(NC(=O)NC4CC4)c(Cl)c3)c2cc1C(N)=O]

or a pharmaceutically acceptable salt thereof; and (iii) (6S,9aS)-N-benzyl-8-({6-[3-(4-ethylpiperazin-1-yl) azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide (E7386) having the structure:

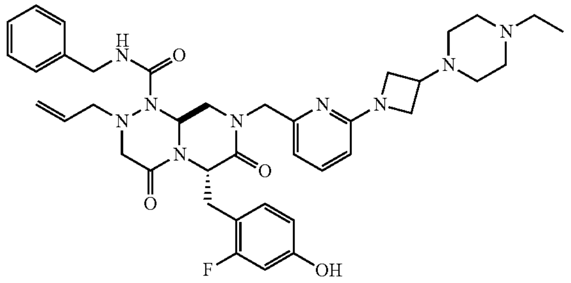

or a pharmaceutically acceptable salt thereof,
wherein the PD-1 antagonist is not atezolizumab.

[2]. The method of [1], wherein the cancer is a solid tumor.

[3]. The method of [1], wherein the cancer is selected from the group consisting of: a renal cell carcinoma (RCC), a colorectal cancer (CRC), a hepatocellular carcinoma (HCC), a melanoma, a bladder cancer, a breast cancer, and a non-small cell lung cancer (NSCLC).

[4]. The method of [1], wherein the cancer is a RCC.

[5]. The method of any one of [1]-[4], wherein the PD-1 antagonist is a monoclonal antibody, or an antigen binding fragment thereof.

[6]. The method of any of [1]-[5], wherein the PD-1 antagonist is an anti-PD-1 antibody.

[7]. The method of any of [1]-[6], wherein the PD-1 antagonist is pembrolizumab or nivolumab.

[8]. The method of any one of [1]-[7], wherein the PD-1 antagonist is pembrolizumab.

[9]. The method of any one of [1]-[8], wherein lenvatinib or a pharmaceutically acceptable salt thereof is administered daily; and pembrolizumab is administered once every three weeks.

[10]. The method of [9], wherein lenvatinib or a pharmaceutically acceptable salt thereof is administered at a daily dose of 24 mg, 20 mg, 18 mg, 12 mg or 8 mg; and pembrolizumab is administered at a dose of 200 mg for adults or 2 mg/kg (up to 200 mg) for pediatrics once every three weeks.

[11]. The method of any of [1]-[10], wherein lenvatinib or a pharmaceutically acceptable salt thereof is lenvatinib mesylate; and E7386 or a pharmaceutically acceptable salt thereof is E7386.

[12]. A pharmaceutical composition for treating a cancer, comprising (6S,9aS)-N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl) hexahydro-2H-pyrazino[2,1-c][1,2,4]triazine-1(6H)-carboxamide (E7386) or a pharmaceutically acceptable salt thereof, wherein E7386 or a pharmaceutically acceptable salt thereof is administered in combination with (a) lenvatinib or a pharmaceutically acceptable salt thereof; and (b) an anti-PD-1 antibody.

[13]. A pharmaceutical composition for treating a cancer, comprising an anti-PD-1 antibody, wherein the an anti-PD-1 antibody is administered in combination with (a) lenvatinib or a pharmaceutically acceptable salt thereof; and (b) (6S,9aS)-N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4] triazine-1(6H)-carboxamide (E7386) or a pharmaceutically acceptable salt thereof.

[14]. A pharmaceutical composition for treating a cancer, comprising lenvatinib or a pharmaceutically acceptable salt thereof wherein lenvatinib or a pharmaceutically acceptable salt thereof is administered in combination with (a) (6S,9aS)-N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl) hexahydro-2H-pyrazino[2,1-c][1,2,4]triazine-1(6H)-carboxamide (E7386) or a pharmaceutically acceptable salt thereof; and (b) an anti-PD-1 antibody.

[15]. The pharmaceutical composition of any of [12]-[14], wherein lenvatinib or a pharmaceutically acceptable salt thereof is lenvatinib mesylate; and E7386 or a pharmaceutically acceptable salt thereof is E7386.

[16]. The pharmaceutical composition of any of [12]-[15], wherein the cancer is a solid tumor.

[17]. The pharmaceutical composition of any of [12]-[15], wherein the cancer is selected from the group consisting of: a renal cell carcinoma (RCC), a colorectal cancer (CRC), a hepatocellular carcinoma (HCC), a melanoma, a bladder cancer, a urothelial cancer, a breast cancer, a non-small cell lung cancer (NSCLC), an endometrial cancer, and a squamous cell carcinoma of head and neck.

[18]. The pharmaceutical composition of [17], wherein the cancer is a RCC.

[19]. The pharmaceutical composition of any of [12]-[18], wherein the PD-1 antagonist is a monoclonal antibody, or an antigen binding fragment thereof.

[20]. The pharmaceutical composition of any of [12]-[18], wherein the PD-1 antagonist is an anti-PD-1 antibody.

[21]. The pharmaceutical composition of any of [12]-[20], wherein the PD-1 antagonist is pembrolizumab or nivolumab.

[22]. The pharmaceutical composition of any of [12]-[21], wherein the PD-1 antagonist is pembrolizumab.

[23]. The pharmaceutical composition of any of [12]-[22], wherein lenvatinib or a pharmaceutically acceptable salt thereof is administered daily; and the PD-1 antagonist is pembrolizumab and is administered once every three weeks.

[24]. The pharmaceutical composition of [23], wherein lenvatinib or a pharmaceutically acceptable salt thereof is administered at a daily dose of 24 mg, 20 mg, 18 mg, 12 mg or 8 mg; and pembrolizumab is administered at a dose of 200 mg for adults or 2 mg/kg (up to 200 mg) for pediatrics once every three weeks.

[25]. The pharmaceutical composition of any of [12]-[24], wherein lenvatinib or a pharmaceutically acceptable salt thereof is lenvatinib mesylate; and E7386 or a pharmaceutically acceptable salt thereof is E7386.

[26]. Use of the pharmaceutical composition of any of [12]-[25] for the manufacture of a medicament for a treatment of cancer.

[27]. The pharmaceutical composition of any of [12]-[25] for use in the treatment of a cancer.

General Methods. Standard methods in molecular biology are described Sambrook, Fritsch and Maniatis (1982 & 1989 $2^{nd}$ Edition, 2001 $3^{rd}$ Edition) Molecular Cloning, A Laboratory Manual, Cold Spring Harbor Laboratory Press, Cold Spring Harbor, N.Y.; Sambrook and Russell (2001) Molecular Cloning, $3^{rd}$ ed., Cold Spring Harbor Laboratory Press, Cold Spring Harbor, N.Y.; Wu (1993) Recombinant DNA, Vol. 217, Academic Press, San Diego, Calif.). Standard methods also appear in Ausbel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) Current Protocols in Protein Science, Vol. 1, John Wiley and Sons, Inc., New York). Chemical analysis, chemical modification, post-translational modification, production of fusion proteins, glycosylation of proteins are described (see, e.g., Coligan, et al. (2000) *Current* Protocols in Protein Science, Vol. 2, John Wiley and Sons, Inc., New York; Ausubel, et al. (2001) Current Protocols in Molecular Biology, Vol. 3, John Wiley and Sons, Inc., NY, N.Y., pp. 16.0.5-16.22.17; Sigma-Aldrich, Co. (2001) Products for Life Science Research, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) Current Protcols in Immunology, Vol. 1, John Wiley and Sons, Inc., New York; Harlow and Lane (1999) Using Antibodies, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) Current Protocols in Immunology, Vol. 4, John Wiley, Inc., New York).

Monoclonal, polyclonal, and humanized antibodies can be prepared (see, e.g., Sheperd and Dean (eds.) (2000) *Monoclonal Antibodies*, Oxford Univ. Press, New York, N.Y.; Kontermann and Dubel (eds.) (2001) *Antibody Engineering*, Springer-Verlag, New York; Harlow and Lane (1988) *Antibodies A Laboratory Manual*, Cold Spring Harbor Laboratory Press, Cold Spring Harbor, N.Y., pp. 139-243; Carpenter, et al. (2000) *J. Immunol.* 165:6205; He, et al. (1998) *J. Immunol.* 160:1029; Tang et al. (1999) J. Biol. Chem. 274:27371-27378; Baca et al. (1997) *J. Biol. Chem.* 272:10678-10684; Chothia et al. (1989) *Nature* 342:877-883; Foote and Winter (1992) *J. Mol. Biol.* 224:487-499; U.S. Pat. No. 6,329,511).

An alternative to antibody humanization is to use human antibody libraries displayed on phage or human antibody libraries in transgenic mice (Vaughan et al. (1996) *Nature* Biotechnol. 14: 309-314; Barbas (1995) *Nature Medicine* 1: 837-839; Mendez et al. (1997) *Nature Genetics* 15: 146-156; Hoogenboom and Chames (2000) *Immunol. Today* 21: 371-377; Barbas et al. (2001) *Phage Display: A Laboratory Manual*, Cold Spring Harbor Laboratory Press, Cold Spring Harbor, N.Y.; Kay et al. (1996) *Phage Display of Peptides and Proteins: A Laboratory Manual*, Academic Press, San Diego, Calif.; de Bruin et al. (1999) *Nature Biotechnol.* 17: 397-399).

Purification of antigen is not necessary for the generation of antibodies. Animals can be immunized with cells bearing the antigen of interest. Splenocytes can then be isolated from the immunized animals, and the splenocytes can fused with a myeloma cell line to produce a hybridoma (see, e.g., Meyaard et al. (1997) *Immunity* 7: 283-290; Wright et al. (2000) *Immunity* 13: 233-242; Preston et al., supra; Kaithamana et al. (1999) *J. Immunol.* 163:5157-5164).

Antibodies can be conjugated, e.g., to small drug molecules, enzymes, liposomes, polyethylene glycol (PEG). Antibodies are useful for therapeutic, diagnostic, kit or other purposes, and include antibodies coupled, e.g., to dyes, radioisotopes, enzymes, or metals, e.g., colloidal gold (see, e.g., Le Doussal et al. (1991) *J. Immunol.* 146: 169-175; Gibellini et al. (1998) *J. Immunol.* 160:3891-3898; Hsing and Bishop (1999) *J. Immunol.* 162: 2804-2811; Everts et al. (2002) *J. Immunol.* 168: 883-889).

Methods for flow cytometry, including fluorescence activated cell sorting (FACS), are available (see, e.g., Owens, et al. (1994) *Flow Cytometry Principles for Clinical Laboratory Practice*, John Wiley and Sons, Hoboken, N.J.; Givan (2001) *Flow Cytometry*, $2^{nd}$ ed.; Wiley-Liss, Hoboken, N.J.; Shapiro (2003) *Practical Flow Cytometry*, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probesy (2003) *Catalogue*, Molecular Probes, Inc., Eugene, OR; Sigma-Aldrich (2003) *Catalogue*, St. Louis, MO).

Standard methods of histology of the immune system are described (see, e.g., Muller-Harmelink (ed.) (1986) *Human Thymus: Histopathology and Pathology*, Springer Verlag, New York, NY; Hiatt, et al. (2000) *Color Atlas of Histology*, Lippincott, Williams, and Wilkins, Phila, PA; Louis, et al. (2002) *Basic Histology: Text and Atlas*, McGraw-Hill, New York, NY).

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, MD); GCG Wisconsin Package (Accelrys, Inc., San Diego, CA); DeCypher® (TimeLogic Corp., Crystal Bay, Nevada); Menne, et al. (2000) *Bioinformatics* 16: 741-742; Menne, et al. (2000) *Bioinformatics Applications Note* 16: 741-742; Wren, et al. (2002) *Comput. Methods Programs Biomed.* 68: 177-181; von Heijne (1983) *Eur. J. Biochem.* 133: 17-21; von Heijne (1986) *Nucleic Acids Res.* 14: 4683-4690).

Table 3 provides a brief description of the sequences in the sequence listing.

TABLE 3

| SEQ ID NO: | Description |
|---|---|
| 1 | hPD-1.08A light chain CDR1 |
| 2 | hPD-1.08A light chain CDR2 |
| 3 | hPD-l-08A light chain CDR3 |
| 4 | hPD-1.08A heavy chain CDR1 |
| 5 | hPD-1.08A heavy chain CDR2 |
| 6 | hPD-1.08A heavy chain CDR3 |
| 7 | hPD-1.09A light chain CDR1 |
| 8 | hPD-1.09A light chain CDR2 |
| 9 | hPD-1.09A light chain CDR3 |
| 10 | 11PD-1.09A heavy chain CDR1 |
| 11 | hPD-1.09A heavy chain CDR2 |
| 12 | hPD-1.09A heavy chain CDR3 |
| 13 | 109A-H heavy chain variable region |
| 14 | 409A-H heavy chain full length |
| 15 | K09A-L-11 light chain variable region |
| 16 | K09A-L-16 light chain variable region |
| 17 | K09A-L-17 light chain variable region |
| 18 | K09A-L-11 light chain full length |
| 19 | K09A-L-16 light chain full length |
| 20 | K09A-L-17 light chain full length |
| 21 | Pembrolizumab Heavy chain |
| 22 | Pembrolizumab Light chain |
| 23 | Nivolumab Heavy chain |
| 24 | Nivolumab light chain |
| 25 | Human PD-L1 |

EXAMPLES

Example 1

Anti-Tumor Effect by Triple Combination of E7386, Lenvatinib and Anti-PD-1 Antibody An Eagle's minimal essential medium (E-MEM) containing 10% fetal bovine serum (FBS) and penicillin/streptomycin (100 unit/mL each) was used to culture a mouse Renal cell carcinoma cell line RAG (ATCC number: CCL-142). Logarithmic growing cells were collected from flasks using Trypsin-EDTA. The suspension of cells was centrifuged to remove the supernatant. Next, Hanks' Balanced Salt Solution (HBSS) was used to prepare a cell suspension having a concentration of $2.5\times10^7$ cells/mL. The cell suspension was subcutaneously transplanted at a dose of 0.1 mL on the right lateral side of the body of each of 7-week-old mice (BALB/cAnNCrlCrlj, female, Charles River Laboratories Japan Inc.). Eight (8) days after the transplantation, an electronic digital caliper (Digimatic™ Caliper; Mitutoyo Corporation) was used to measure the short and long diameters of a tumor of interest. The following equations were used to calculate the tumor volume TV and RTV.

$$\text{Tumor Volume TV (mm}^3\text{)=Long Diameter (mm)}\times\text{Short Diameter (mm)}\times\text{Short Diameter (mm)/2} \quad \text{EQ. 1:}$$

$$\text{Relative Tumor Volume RTV=TV on day n/TV on day1} \quad \text{EQ. 2:}$$

Based on the tumor volumes on the first day of administration, grouping was carried out such that the average values of the tumor volumes were almost the same. A 1 mg/ml solution of lenvatinib was prepared using 3 mM HCl and was orally administered at a dose of 0.2 mL/20 g mouse body weight once daily for 28 days. 0.2 mL of an administration sample containing 1.0 mg/mL of an anti-mouse-PD-1 antibody (Clone: RMP1-14, BioXCell, Catalog #: BE0146), which had been diluted with PBS, was intraperitoneally administered (at a dosage of 200 μg/mouse) twice a week a total of 8 times (day 1, day 4, day 8, day 11, day 15, day 18, day 22, and day 25, with the day of the grouping set to day 1). A 2.5 mg/ml solution of E7386 was prepared using 0.1 M HCl and was orally administered at a dose of 0.2 mL/20 g mouse body weight once daily for 28 days. To the control group, nothing was administered. Each group including 8 mice was used to conduct the experiment. Twice a week (day 1, day 4, day 8, day 11, day 15, day 18, day 22, day 25, and day 29), the respective tumor volumes (TV) were determined for the control group, the lenvatinib administration group, the anti-mouse-PD-1 antibody administration group, lenvatinib+anti-mouse-PD-1 antibody administration group, E7386+lenvatinib administration group and triple combination group. The values obtained by logarithmically transforming the tumor volumes were used to carry out statistical analysis by repeated measured Dunnet's multiple comparison. E7386 is (6S,9aS)-N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl) hexahydro-2H-pyrazino[2,1-c][1,2,4]triazine-1(6H)-carboxamide.

In the subcutaneous (s.c.) RAG transplantation model, the triple combination of E7386, lenvatinib and the anti-mouse-PD-1 antibody exhibited a significantly higher anti-tumor effect than either of the dual combinations (i.e., Lenvatinib+Anti PD-1 antibody combination or the lenvatinib+E7386 combination) or each agent when administered alone as a monotherapy. For example, at day 29, the triple combination group had greater than 200 fold less tumor volume compared to the control group and the E7386 group. The triple combination had over 30 fold less and 120 fold less tumor volume compared to the lenvatinib group and anti PD-1 antibody group, respectively. In addition, the triple combination group had greater than 9 fold less and 17 fold less tumor volume compared to the lenvatinib+anti PD-1 antibody combination group and E7386+lenvatinib combination group, respectively.

In the aspect of CR rate, the rate observed with the triple combination group (lenvatinib, pembrolizumab and E7386) was superior to rates observed with the other treatment groups (CR rate: 0, 0, 2, 1, 4, 1, and 7 out of 8 mice in control group, lenvatinib group, anti-PD-1 antibody group, E7386 group, lenvatinib+Anti PD-1 antibody group, E7386+lenvatinib group and Triple combination group, respectively).

Figure 9:
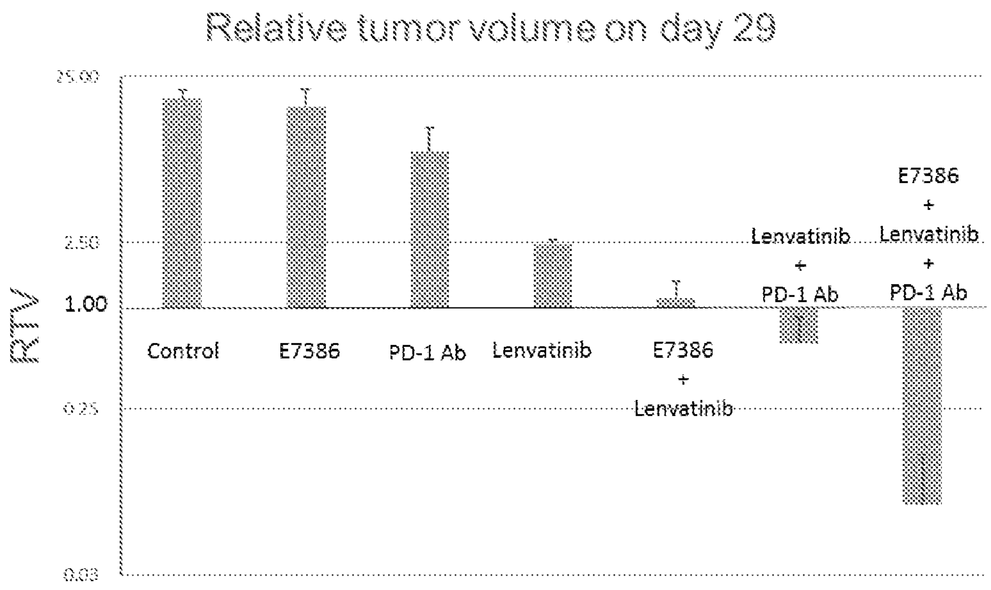
FIG. 9 shows relative tumor volume of each group as shown in FIG. 8 on day 29. Data are shown as means±SE.
Figure 12A:
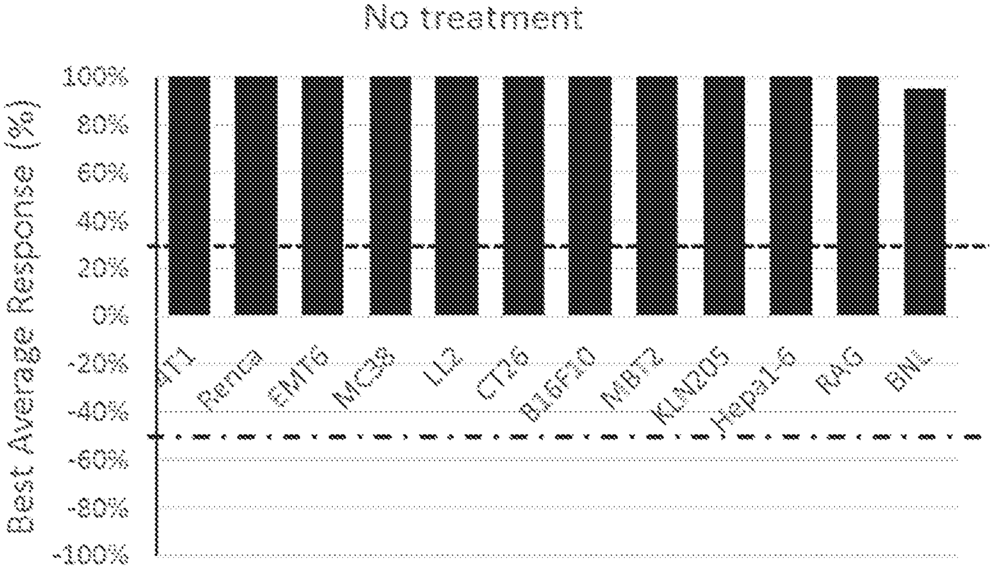
FIGS. 12A to 12G show waterfall graphs showing the Best Average Response (%), which is defined as described in Example 2
Figure 12B:
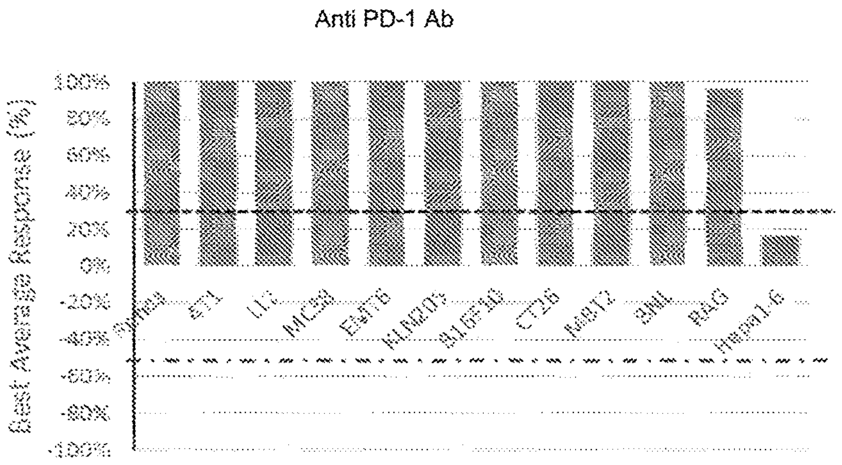
Figure 12C:
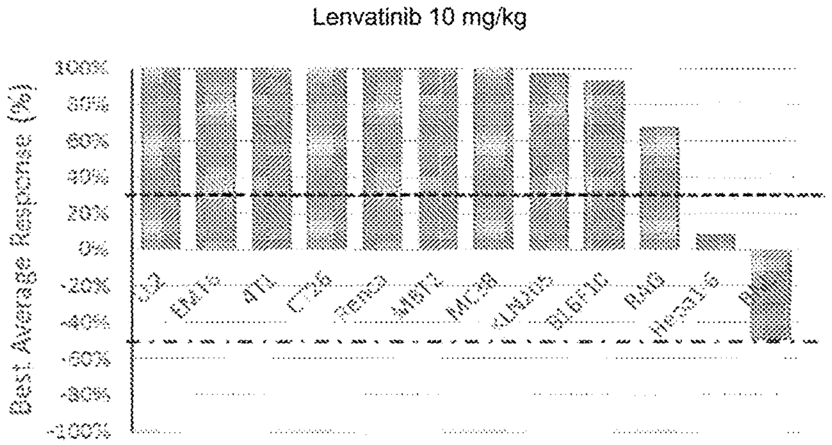
Figure 12D:
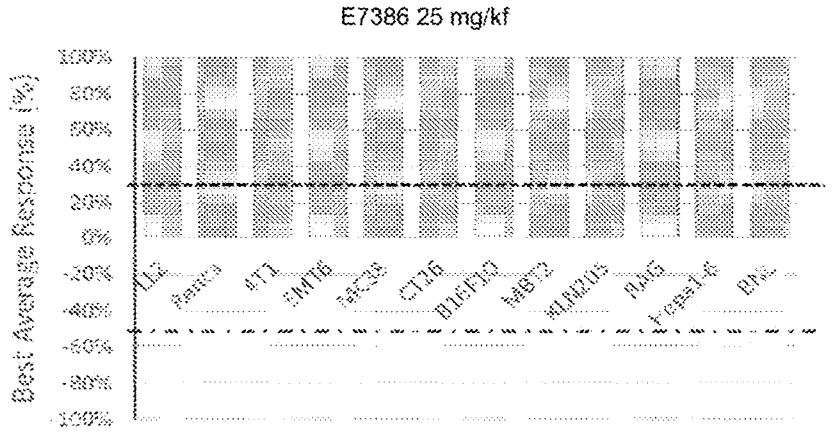
Figure 12E:
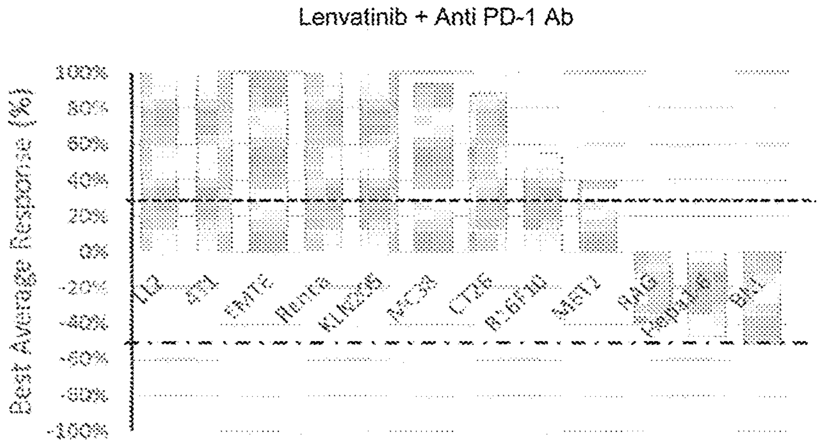
Figure 12F:
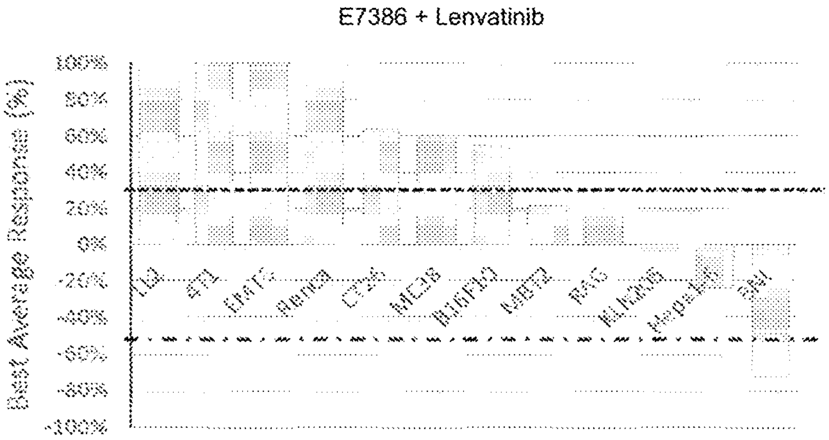
Figure 12G:
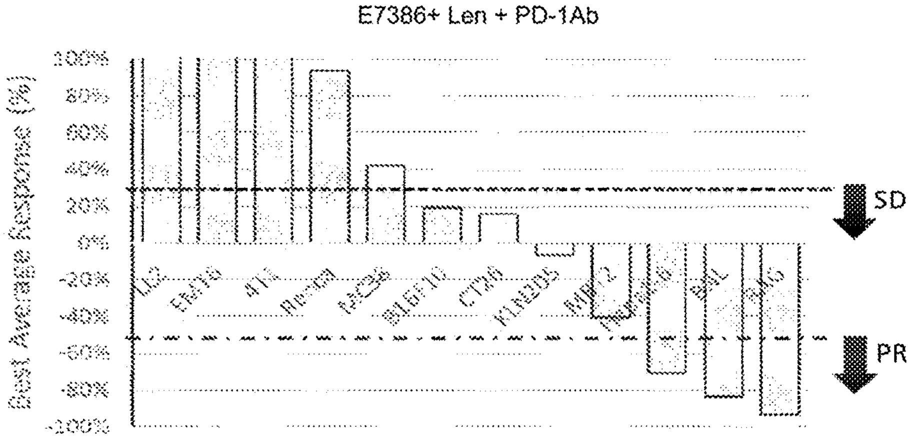

The daily change in the tumor volume is shown in Table 4. In addition, the time course of the tumor volumes change during administration and the relative tumor volume at day 29 of each group are shown in FIG. 8 and FIG. 9, respectively.

TABLE 4

| | Day 1 | Day 4 | Day 8 | Day 11 | Day 15 | Day 18 | Day 22 | Day 25 | Day 29 |
|---|---|---|---|---|---|---|---|---|---|
| Control group | 62 | 93 | 152 | 297 | 419 | 618 | 822 | 1101 | 1160 |
| Lenvatinib group | 62 | 82 | 102 | 134 | 152 | 175 | 162 | 166 | 151 |
| Anti-PD-1 antibody group | 62 | 86 | 124 | 165 | 222 | 274 | 347 | 414 | 482 |

TABLE 4-continued

| | Day 1 | Day 4 | Day 8 | Day 11 | Day 15 | Day 18 | Day 22 | Day 25 | Day 29 |
|---|---|---|---|---|---|---|---|---|---|
| E7386 group | 62 | 93 | 148 | 210 | 301 | 408 | 588 | 723 | 923 |
| Lenvatinib + Anti PD-1 antibody dual combination group | 62 | 73 | 78 | 92 | 86 | 72 | 58 | 49 | 38 |
| E7386 + Lenvatinib dual combination group | 62 | 70 | 74 | 83 | 84 | 83 | 78 | 71 | 68 |
| Triple combination group | 62 | 70 | 61 | 55 | 31 | 21 | 12 | 7 | 4 |

Example 2

Anti-Tumor Effect by Triple Combination of E7386, Lenvatinib and Anti-PD-1 Antibody Various culture mediums were used to culture a mouse cell lines (see FIGS. 10A-10C, column A). Logarithmic growing cells were collected from flasks using Trypsin-EDTA. The suspension of cells was centrifuged to remove the supernatant. Next, Hanks' Balanced Salt Solution (HBSS) was used to prepare a cell suspension having a certain cell concentration (see FIGS. 10A-10C, column B). The cell suspension was subcutaneously transplanted at a dose of 0.1 mL on the right lateral side of the body of each of 7-week-old immune competent mice (see FIGS. 10A-10C, column C).

Several days after the transplantation (see FIGS. 10A-10C, column D), an electronic digital caliper (Digimatic™ Caliper; Mitutoyo Corporation) was used to measure the short and long diameters of a tumor in the animal. The following equations were used to calculate the tumor volume TV and RTV.

Tumor Volume TV (mm3)=Long Diameter (mm)×Short Diameter (mm)×Short Diameter (mm)/2 EQ. 1:

Relative Tumor Volume RTV=TV on day n/TV on day1 EQ. 2:

Based on the tumor volumes on the first day of administration, grouping was carried out such that the average values of the tumor volumes were almost the same. A 1 mg/ml solution of lenvatinib was prepared using 3 mM HCl and was orally administered at a dose of 0.2 mL/20 g mouse body weight once daily for 28 days. 0.2 mL of an administration sample containing 1.0 mg/mL of an anti-mouse-PD-1 antibody (Clone: RMP1-14, BioXCell, Catalog #: BE0146), which had been diluted with PBS, was intraperitoneally administered (at a dosage of 200 μg/mouse) twice a week for 3 or 4 weeks (see FIGS. 10A-10C, column E). A 2.5 mg/ml solution of E7386 was prepared using 0.1 M HCl and was orally administered at a dose of 0.2 mL/20 g mouse body weight once daily for 3 or 4 weeks (see FIGS. 10A-10C, column E). To the control group, nothing was administered. Each group including 8 mice was used to conduct the experiment. Twice a week for 3 or 4 weeks (see FIGS. 10A-10C, column E), the respective tumor volumes (TV) were determined for the control group, the lenvatinib administration group, the anti-mouse-PD-1 antibody administration group, the lenvatinib+anti-mouse-PD-1 antibody administration group, the E7386+lenvatinib administration group and the triple combination therapy group. The values obtained by logarithmically transforming the tumor volumes were used to carry out statistical analysis by repeated measured Dunnet's multiple comparison. E7386 is (6S,9aS)-N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide.

As shown in FIG. 11 and FIGS. 12A-12G, the triple combination therapy of E7386, lenvatinib and the anti-mouse-PD-1 antibody exhibited a higher anti-tumor effect than either of the dual combinations (i.e., Lenvatinib+Anti PD-1 antibody combination or the lenvatinib+E7386 combination) or each agent when administered alone as a monotherapy.

Relative tumor volume (RTV) at time t was calculated following formula:

$RTV=TV_t/TV_{initial}\times 100\%$ EQ. 3:

We defined the Best Average Response (BestAvgResponse) as the minimum value of the average of (RTV-100%) for t≥8 d (EQ. 4). This metric captures a combination of speed, strength and durability of response into a single value. The criteria for response (mRECIST) were adapted from RECIST criteria and defined as follows (applied in this order): mCR, BestAvgResponse<−95%; mPR, BestAvgResponse<−50%; mSD, BestAvgResponse<30%; mPD, not otherwise categorized.

REFERENCES

1. Sharpe, A. H, Wherry, E. J., Ahmed R., and Freeman G. J. The function of programmed cell death 1 and its ligands in regulating autoimmunity and infection. *Nature Immunology* (2007); 8:239-245.
2. Dong H et al. Tumor-associated B7-H1 promotes T-cell apoptosis: a potential mechanism of immune evasion. Nat Med. 2002 August; 8(8):793-800.
3. Yang et al. PD-1 interaction contributes to the functional suppression of T-cell responses to human uveal melanoma cells in vitro. *Invest Ophthalmol Vis Sci.* 2008 June; 49(6 (2008): 49: 2518-2525.
4. Ghebeh et al. The B7-H1 (PD-L1) T lymphocyte-inhibitory molecule is expressed in breast cancer patients with infiltrating ductal carcinoma: correlation with important high-risk prognostic factors. *Neoplasia* (2006) 8: 190-198.
5. Hamanishi J et al. Programmed cell death 1 ligand 1 and tumor-infiltrating CD8+ T lymphocytes are prognostic factors of human ovarian cancer. *Proceeding of the National Academy of Sciences* (2007): 104: 3360-3365.
6. Thompson R H et al. Significance of B7-H1 overexpression in kidney cancer. Clinical genitourin *Cancer* (2006): 5: 206-211.
7. Nomi, T. Sho, M., Akahori, T., et al. Clinical significance and therapeutic potential of the programmed death-1 ligand/programmed death-1 pathway in human pancreatic cancer. *Clinical Cancer Research* (2007); 13:2151-2157.
8. Ohigashi Y et al. Clinical significance of programmed death-1 ligand-1 and programmed death-1 ligand 2 expression in human esophageal cancer. *Clin. Cancer Research* (2005): 11: 2947-2953.
9. Inman et al. PD-L1 (B7-H1) expression by urothelial carcinoma of the bladder and BCG-induced granulomata: associations with localized stage progression. *Cancer* (2007): 109: 1499-1505.
10. Shimauchi T et al. Augmented expression of programmed death-1 in both neoplasmatic and nonneoplastic CD4+ T-cells in adult T-cell Leukemia/Lymphoma. *Int. J. Cancer* (2007): 121:2585-2590.
11. Gao et al. Overexpression of PD-L1 significantly associates with tumor aggressiveness and postoperative recurrence in human hepatocellular carcinoma. *Clinical Cancer Research* (2009) 15: 971-979.
12. Nakanishi J. Overexpression of B7-H1 (PD-L1) significantly associates with tumor grade and postoperative prognosis in human urothelial cancers. *Cancer Immunol Immunother*. (2007) 56: 1173-1182.
13. Hino et al. Tumor cell expression of programmed cell death-1 is a prognostic factor for malignant melanoma. *Cancer* (2010): 00: 1-9.
14. Ghebeh H. Foxp3+ tregs and B7-H1+/PD-1+ T lymphocytes co-infiltrate the tumor tissues of high-risk breast cancer patients: implication for immunotherapy. *BMC Cancer.* 2008 Feb. 23; 8: 57.
15. Ahmadzadeh M et al. Tumor antigen-specific CD8 T cells infiltrating the tumor express high levels of PD-1 and are functionally impaired. *Blood* (2009) 114: 1537-1544.
16. Thompson R H et al. PD-1 is expressed by tumor infiltrating cells and is associated with poor outcome for patients with renal carcinoma. *Clinical Cancer Research* (2007) 15: 1757-1761.
17. US Patent Application Publication No. 2018-0185395.
18. Canadian Application No. 3 044 658.
19. U.S. Pat. No. 9,174,998.
20. U.S. Pat. No. 10,259,817.
21. Keiichi Tamai, et al., "Suppressive expression of CD274 increases tumorigenesis and cancer stem cell phenotypes in cholangiocarcinoma," *Cancer Sci.* 105 (6): 667-674, 2014. Anthony B. El-Khoueiry, et al., "A phase I first-in-human study of PRI-724 in patients (pts) with advanced solid tumors," *J. Clin. Oncol.* 31 (15_supple (May 20, 2013)): abstr2501.
22. Renée van Amerongen, et al., "Break the loop, escape the cycle?" *The EMBO Journal* 2013, 32: 19774989.

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

What is claimed:

1. A method for treating a cancer in a human subject comprising administering to the human subject a combination therapy which comprises:

(i) an antagonist of a Programmed Death 1 protein (PD-1) which is an anti-PD-1 antibody;

(ii) lenvatinib having the structure:

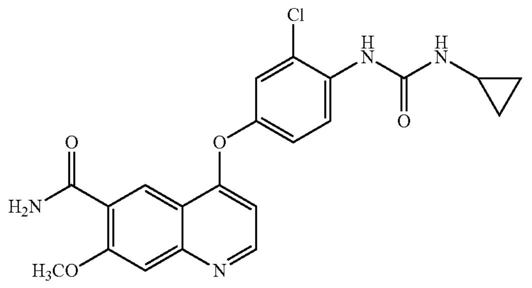 [SMILES: COc1cc2nccc(Oc3ccc(NC(=O)NC4CC4)c(Cl)c3)c2cc1C(N)=O]

or a pharmaceutically acceptable salt thereof, wherein the lenvatinib is administered daily; and (iii) (6S,9aS)-N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide (E7386) having the structure:

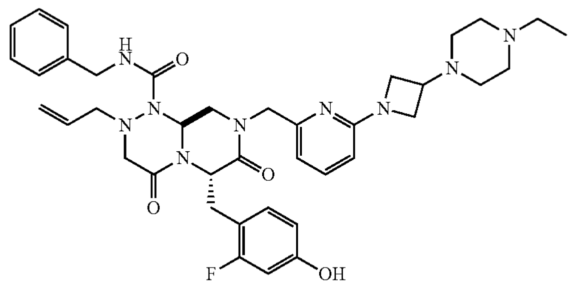

or a pharmaceutically acceptable salt thereof, wherein the cancer is selected from the group consisting of: a renal cell carcinoma (RCC), a colorectal cancer (CRC), a hepatocellular carcinoma (HCC), a melanoma, and a bladder cancer.

2. The method of claim 1, wherein the cancer is a RCC.

3. The method of claim 1, wherein the anti-PD-1 antibody is pembrolizumab or nivolumab.

4. The method of claim 1, wherein the anti-PD-1 antibody is pembrolizumab.

5. The method of claim 1, wherein lenvatinib or a pharmaceutically acceptable salt thereof is administered daily; and pembrolizumab is administered once every three weeks.

6. The method of claim 5, wherein lenvatinib or a pharmaceutically acceptable salt thereof is administered at a daily dose of 24 mg, 20 mg, 18 mg, 12 mg or 8 mg; and pembrolizumab is administered at a dose of 200 mg for an adult human subject or 2 mg/kg up to 200 mg for a pediatric human subject once every three weeks.

7. The method of claim 1, wherein lenvatinib or a pharmaceutically acceptable salt thereof is lenvatinib mesylate; and E7386 or a pharmaceutically acceptable salt thereof is E7386.

8. The method of claim 1, wherein lenvatinib or a pharmaceutically acceptable salt thereof is administered daily; and the anti-PD-1 antibody is pembrolizumab and is administered once every six weeks.

9. The method of claim 8, wherein lenvatinib or a pharmaceutically acceptable salt thereof is administered at a daily dose of 24 mg, 20 mg, 18 mg, 12 mg or 8 mg; and pembrolizumab is administered at a dose of 400 mg once every six weeks.

* * * * *